US012773564B2

(12) United States Patent
Badie et al.

(10) Patent No.: US 12,773,564 B2
(45) Date of Patent: Oct. 27, 2026

(54) METHOD AND SYSTEM FOR DYNAMIC ATRIOVENTRICULAR DELAY WITH ADAPTIVE SEARCH AND RATE-RESPONSIVE SEARCH EXTENSION

(71) Applicant: Pacesetter, Inc., Sylmar, CA (US)

(72) Inventors: Nima Badie, Gold River, CA (US); Aditya Goil, Stevenson Ranch, CA (US); Kunal Chaniary, Porter Ranch, CA (US)

(73) Assignee: Pacesetter, Inc., Sylmar (CA)

( * ) Notice: Subject to any disclaimer, the term of this patent is extended or adjusted under 35 U.S.C. 154(b) by 209 days.

(21) Appl. No.: 18/543,165

(22) Filed: Dec. 18, 2023

(65) Prior Publication Data

US 2024/0252827 A1 Aug. 1, 2024

Related U.S. Application Data

(60) Provisional application No. 63/482,593, filed on Feb. 1, 2023.

(51) Int. Cl.
*A61N 1/365* (2006.01)
*A61N 1/368* (2006.01)

(52) U.S. Cl.
CPC ....... *A61N 1/3682* (2013.01); *A61N 1/36535* (2013.01); *A61N 1/36542* (2013.01); *A61N 1/36592* (2013.01)

(58) Field of Classification Search
CPC .............. A61N 1/3682; A61N 1/36535; A61N 1/36542; A61N 1/36592; A61B 5/283; A61B 5/29
See application file for complete search history.

(56) References Cited

U.S. PATENT DOCUMENTS 6,832,112 B1 12/2004 Bornzin
6,928,326 B1 8/2005 Levine
(Continued)

FOREIGN PATENT DOCUMENTS

WO 2017074999 A1 5/2017

OTHER PUBLICATIONS

Extended European Search Report for corresponding EP Application No. 24150195.6 dated Sep. 10, 2024 (14 pages).
(Continued)

*Primary Examiner* — Benjamin J Klein
*Assistant Examiner* — Elizabeth L Okonak
(74) *Attorney, Agent, or Firm* — Dean D. Small; Carroll, Hoette & Butscher, LLC

(57) ABSTRACT

An implantable medical device (IMD) and process are provided comprising one or more electrodes configured to be implanted to define a pacing vector through at least a portion of a ventricle. Sensing circuitry is configured to sense intrinsic atrial activity (As) and intrinsic ventricular activity (Vs). A pulse generator (PG) if provided, and memory configured to store program instructions and an atrioventricular delay search parameter ($AVD_{SEARCH}$). The $AVD_{SEARCH}$ is an interval of time. One or more processors, that when executing the program instructions, is configured to direct the PG to deliver ventricular pacing pulses based on an atrioventricular delay (AVD) and periodically initiate an AVD search operation utilizing the $AVD_{SEARCH}$. A heart rate is determined and compared to a threshold. Responsive to determining that the heart rate exceeds the threshold, the $AVD_{SEARCH}$ is reduced, and cardiac activity is detected during the AVD search operation utilizing the reduced $AVD_{SEARCH}$.

20 Claims, 6 Drawing Sheets

(56) References Cited

U.S. PATENT DOCUMENTS

| | | | |
|---|---|---|---|
| 7,139,609 B1 | 11/2006 | Min et al. | |
| 7,509,170 B2 | 3/2009 | Zhang et al. | |
| 7,643,878 B1 | 1/2010 | Muller et al. | |
| 7,702,390 B1 | 4/2010 | Min | |
| 7,778,706 B1 | 8/2010 | Min | |
| 7,941,217 B1 | 5/2011 | Pei et al. | |
| 8,214,041 B2 | 7/2012 | Gelder et al. | |
| 8,391,980 B2 | 3/2013 | Bornzin et al. | |
| 8,442,634 B2 | 5/2013 | Min et al. | |
| 8,565,880 B2 | 10/2013 | Dong et al. | |
| 8,831,747 B1 | 9/2014 | Min et al. | |
| 9,044,610 B2 | 6/2015 | Rosenberg et al. | |
| 9,216,285 B1 | 12/2015 | Boling et al. | |
| 9,232,485 B2 | 1/2016 | Wu et al. | |
| 9,333,351 B2 | 5/2016 | Arnold et al. | |
| 10,173,066 B2 | 1/2019 | Wisnoskey et al. | |
| 10,569,091 B2 | 2/2020 | Badie et al. | |
| 10,582,874 B2 | 3/2020 | Badie et al. | |
| 10,589,100 B2 | 3/2020 | Min et al. | |
| 10,668,289 B2 | 6/2020 | Min | |
| 11,154,719 B2 | 10/2021 | Badie et al. | |
| 11,207,525 B2 | 12/2021 | Badie et al. | |
| 11,273,312 B2 | 3/2022 | Badie et al. | |
| 11,311,733 B2 | 4/2022 | Wisnoskey | |
| 11,400,297 B2 | 8/2022 | Muller et al. | |
| 2004/0147966 A1 | 7/2004 | Ding et al. | |
| 2004/0193323 A1 | 9/2004 | Kramer et al. | |
| 2005/0013147 A1 | 1/2005 | Villablanca | |
| 2005/0043895 A1 | 2/2005 | Schechter | |
| 2005/0131476 A1 | 6/2005 | Kim et al. | |
| 2005/0209649 A1 | 9/2005 | Ferek-petric | |
| 2006/0047320 A1 | 3/2006 | Ding et al. | |
| 2006/0235478 A1 | 10/2006 | Van Gelder et al. | |
| 2006/0235481 A1 | 10/2006 | Fogoros et al. | |
| 2008/0140147 A1 | 6/2008 | Husby | |
| 2008/0269826 A1 | 10/2008 | Lian et al. | |
| 2009/0005832 A1 | 1/2009 | Zhu et al. | |
| 2009/0163973 A1 | 6/2009 | Meyer et al. | |
| 2009/0234411 A1 | 9/2009 | Sambelashvili et al. | |
| 2009/0234414 A1 | 9/2009 | Sambelashvili et al. | |
| 2009/0281591 A1 | 11/2009 | Shuros et al. | |
| 2010/0069987 A1 | 3/2010 | Min et al. | |
| 2010/0145405 A1 | 6/2010 | Min et al. | |
| 2010/0222834 A1 | 9/2010 | Sweeney et al. | |
| 2011/0098772 A1 | 4/2011 | Min | |
| 2011/0137369 A1 | 6/2011 | Ryu et al. | |
| 2012/0004697 A1 | 1/2012 | Ternes et al. | |
| 2012/0165892 A1 | 6/2012 | Min et al. | |
| 2013/0296962 A1 | 11/2013 | Keel et al. | |
| 2014/0207013 A1 | 7/2014 | Lian et al. | |
| 2015/0283385 A1 | 10/2015 | Sambelashvili et al. | |
| 2016/0051821 A1* | 2/2016 | Sambelashvili | A61N 1/3682 607/17 |
| 2016/0129263 A1* | 5/2016 | Demmer | A61N 1/37205 607/17 |
| 2017/0028203 A1* | 2/2017 | Ghosh | A61B 5/29 |
| 2017/0119273 A1 | 5/2017 | Thakur et al. | |
| 2017/0246460 A1 | 8/2017 | Ghosh | |
| 2019/0009095 A1* | 1/2019 | Sheldon | A61N 1/37205 |
| 2019/0111270 A1* | 4/2019 | Zhou | A61B 5/283 |
| 2020/0046312 A1 | 2/2020 | Min et al. | |
| 2020/0094057 A1* | 3/2020 | Badie | A61N 1/36592 |
| 2020/0188677 A1* | 6/2020 | An | A61N 1/36592 |
| 2022/0008724 A1 | 1/2022 | Badie et al. | |
| 2022/0218999 A1 | 7/2022 | Wisnoskey | |

OTHER PUBLICATIONS

Partial Europe Search Report for corresponding EP Application No. 24150195.6-1122 dated Jul. 3, 2024 (15 pages).

Varma et al. "Programming cardiac resynchronization therapy for electrical synchrony: reaching beyond left bundle branch block and left ventricular activation delay" Journal of the Americal ?Heart Association; 2018 (13 pages).

ISRWO for corresponding Application No. PCT/US2019/051949 dated Dec. 11, 2019 (16 pages).

ISRWO for corresponding Application No. PCT/US2019/051946 dated Dec. 5, 2019 (16 pages).

Ghosh et al. "Auotmated detection of effective left-ventricular pacing: going beyond percentage pacing counters" Eurospace; 2015 (8 pages).

Correspondence for EP Application No. 18214078.0-1122 dated Jul. 1, 2021 (5 pages).

Extended European Search Report for corresponding EP Application No. 18186494.3-1124 dated Oct. 8, 2018 (7 pages).

* cited by examiner

METHOD AND SYSTEM FOR DYNAMIC ATRIOVENTRICULAR DELAY WITH ADAPTIVE SEARCH AND RATE-RESPONSIVE SEARCH EXTENSION

CROSS-REFERENCE TO RELATED APPLICATIONS

This application claims priority to U.S. Provisional Patent Application No. 63/482,593, filed 1 Feb. 2023, entitled "METHOD AND SYSTEM FOR DYNAMIC ATRIOVENTRICULAR DELAY WITH ADAPTIVE SEARCH AND RATE-RESPONSIVE SEARCH EXTENSION", the subject matter of which is incorporated herein by reference in its entirety.

FIELD OF THE INVENTION

Embodiments herein generally relate to implantable medical devices, and more particularly to minimizing the amount of search time used to determine a measured intrinsic conduction time.

BACKGROUND OF THE INVENTION

Advances in implantable medical devices (IMD) and left ventricular (LV) lead design have improved electrical stimulation, delays, and pacing, resulting in a better patient outcome. Loss of atrioventricular (AV) electrical and mechanical synchrony can result in inadequate ventricular depolarization, leading to suboptimal therapy. Optimal AV delay (AVD) can improve electrical synchrony by fusing an intrinsic conduction wavefront and device pacing to produce an enhanced depolarization of the ventricles and increased cardiac output.

Cardiac resynchronization therapy (CRT) has been shown to improve hemodynamics in heart failure (HF) patients, particularly when the AVD has been individualized for each patient. AVD programming for each patient is commonly performed in-clinic at implant, when an AVD is selected for each patient based on echocardiographic, ECG, or blood pressure metrics. This one-time, static AVD selection does not account for short-term changes (hourly; e.g., exercise, sleep) or long-term changes (monthly; e.g., disease progression) in a patient's electromechanical conduction after the patient leaves the clinic.

At least one approach has been proposed that adjusts the AVD over time. In this conventional approach, an intrinsic PR interval (e.g., interval from onset of P-wave to start of QRS complex) is measured and the AVD is set to equal the PR interval reduced by a fixed amount that the clinician programs. In order to measure the PR interval, the AVD is prolonged periodically, such as every 4-5 minutes or every 200-300 beats, to a longer $AVD_{SEARCH}$ value (e.g., 350/325 ms paced/sensed AVD) for up to 5 beats, for example. This extension allows a ventricular sensed event to occur and the intrinsic PR interval to be measured. The new AVD is set to the updated PR interval, abbreviated by a programmable offset (e.g., PR interval—30%).

One complaint is that the $AVD_{SEARCH}$ is unphysiologically long for up to 2% of beats (e.g., 5 beats of every 256 beats). The long $AVD_{SEARCH}$ values can yield suboptimal filling of the ventricles and, thus, suboptimal blood ejection from the heart.

A need remains for methods and systems that provide dynamic AV timing adjustment that minimizes the unphysiological aspects that occur during the search window for the intrinsic PR interval.

SUMMARY

In accordance with embodiments herein, an implantable medical device (IMD) is provided comprising one or more electrodes, sensing circuitry, a pulse generator (PG), memory, and one or more processors. The one or more electrodes are configured to be implanted to define a pacing vector through at least a portion of a ventricle. The sensing circuitry is configured to sense intrinsic atrial activity (As) and intrinsic ventricular activity (Vs). The memory is configured to store program instructions and an atrioventricular delay search parameter ($AVD_{SEARCH}$), wherein the $AVD_{SEARCH}$ is an interval of time. The one or more processors, when executing the program instructions, is configured to direct the PG to deliver ventricular pacing pulses based on an atrioventricular delay (AVD), periodically initiate an AVD search operation utilizing the $AVD_{SEARCH}$, determine a heart rate, compare the heart rate to a threshold, responsive to determining that the heart rate exceeds the threshold, reduce the $AVD_{SEARCH}$, and detect cardiac activity during the AVD search operation utilizing the reduced $AVD_{SEARCH}$.

Optionally, the $AVD_{SEARCH}$ is reduced by a predetermined duration for every beat per minute (bpm) that the heart rate exceeds the threshold, and the predetermined duration is stored in the memory. Optionally, the one or more processors is further configured to store a rate-responsive sensitivity in the memory, wherein the $AVD_{SEARCH}$ is reduced based on the rate-responsive sensitivity. Optionally, wherein the cardiac activity includes the Vs, and wherein the one or more processors is further configured to, in response to identifying that fewer than a select number of cardiac beats exhibit the Vs during the AVD search operation, increase the reduced $AVD_{SEARCH}$.

Optionally, the one or more processors is further configured to identify whether the cardiac activity detected during the AVD search operation is indicative of a conduction block condition or non-conduction block condition, and, in response to identifying the non-conduction block condition for a consecutive predetermined number of times, reduce the reduced $AVD_{SEARCH}$. Optionally, the one or more processors is further configured to identify an intrinsic PR interval associated with the heart rate, and set the reduced $AVD_{SEARCH}$ to a greater one of i) the reduced $AVD_{SEARCH}$ and ii) the intrinsic PR interval plus a buffer length of time. Optionally, the one or more processors is further configured to identify an intrinsic PR interval associated with the current heart rate, and set the reduced $AVD_{SEARCH}$ based on a comparison of the reduced $AVD_{SEARCH}$ and the intrinsic PR interval.

Optionally, the one or more processors is further configured to identify whether the cardiac activity detected during the AVD search operation is indicative of a conduction block condition or non-conduction block condition, and in response to identifying the conduction block condition, extend the reduced $AVD_{SEARCH}$. In some cases, the one or more processors is further configured to extend the reduced $AVD_{SEARCH}$ up to a rate-dependent maximum.

In accordance with embodiments herein, a method for minimizing an atrioventricular delay search parameter ($AVD_{SEARCH}$) comprises providing one or more electrodes configured to be implanted to define a pacing vector through at least a portion of a ventricle, providing sensing circuitry configured to sense intrinsic atrial activity (As) and intrinsic ventricular activity (Vs), and providing a memory configured to store program instructions and an $AVD_{SEARCH}$, wherein the $AVD_{SEARCH}$ is an interval of time. The method utilizes one or more processors, in an implantable medical device (IMD), that when executing the program instructions, is configured for determining a current heart rate, comparing the heart rate to a threshold, responsive to determining that the heart rate exceeds the threshold, reducing the $AVD_{SEARCH}$, and detecting cardiac activity during an AVD search operation utilizing the reduced $AVD_{SEARCH}$.

Optionally, $AVD_{SEARCH}$ is reduced by a predetermined number of milliseconds (ms) for every beat per minute (bpm) that the heart rate exceeds the threshold. Optionally, the method further comprising storing a rate-responsive sensitivity in the memory, wherein the $AVD_{SEARCH}$ is reduced based on the rate-responsive sensitivity, wherein the rate-responsive sensitivity is programmable.

Optionally, wherein the cardiac activity includes the Vs, the method further comprising identifying a number of sensed ventricular events associated with the Vs detected during the AVD search operation, and, in response to identifying that fewer than a select number of the sensed ventricular events are identified, increasing the reduced $AVD_{SEARCH}$. Optionally, the method further comprising identifying whether the cardiac activity detected during the AVD search operation is indicative of a conduction block condition or a non-conduction block condition, and, in response to identifying the non-conduction block condition, reducing the extended $AVD_{SEARCH}$.

In accordance with embodiments herein, a system comprises one or more electrodes, sensing circuitry, a pulse generator (PG), memory and one or more processors. The one or more electrodes are configured to be implanted to define a pacing vector through at least a portion of a ventricle. The sensing circuitry is configured to sense intrinsic atrial activity (As) and intrinsic ventricular activity (Vs). The memory is configured to store program instructions. The one or more processors, that when executing the program instructions, is configured to direct the PG to deliver ventricular pacing pulses based on an atrioventricular delay (AVD), periodically initiate an AVD search operation in which the AVD is extended, monitor one or more interval stability characteristics, and suspend the AVD search operation based on the one or more interval stability characteristics.

Optionally, the interval stability characteristics include i) heart rate (HR), ii) HR variability, iii) posture, or iv) activity. Optionally, the system further comprises a physiological sensor configured to acquire data associated with at least one of the posture and activity. Optionally, the one or more interval stability characteristics is a stability characteristic of a PR interval.

Optionally, wherein the interval stability characteristics include a heart rate, the one or more processors is configured to determine the heart rate, and compare the heart rate to a heart rate threshold stored in the memory, wherein the AVD search operation is suspended when the heart rate is below the heart rate threshold. Optionally, wherein the interval stability characteristics include a heart rate variability, the one or more processors is configured to determine the heart rate variability, and compare the heart rate variability to a heart rate variability threshold stored in the memory, wherein the AVD search operation is suspended when the heart rate variability is below the heart rate variability threshold.

DETAILED DESCRIPTION

Figure 1:
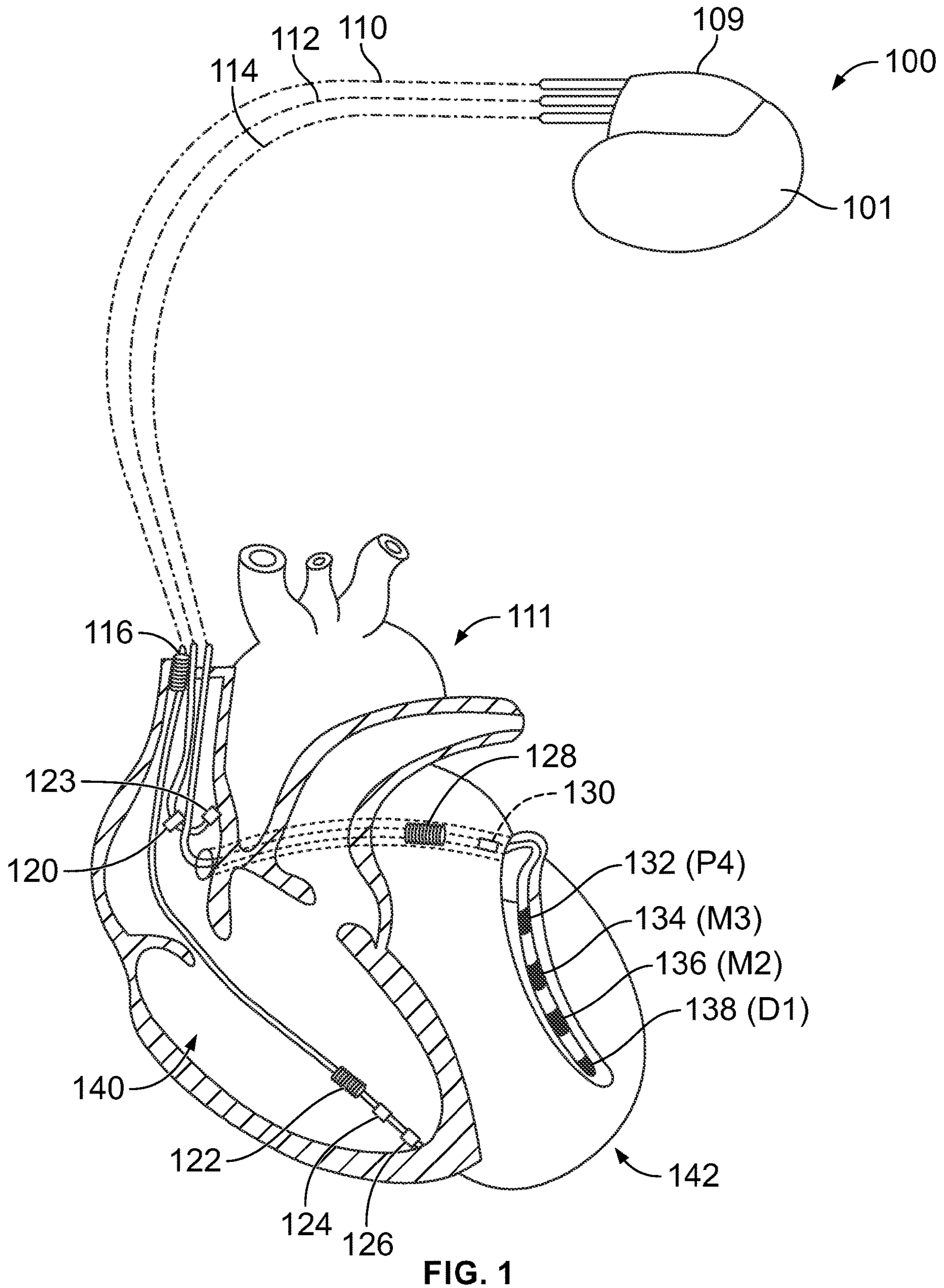
FIG. 1 illustrates an implantable medical device (IMD) in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that other methods may be used in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term “As-Vs interval” shall mean a measured intrinsic conduction time from a sensed atrial (As) event to a sensed ventricular (Vs) event. The sensed ventricular event may be a right ventricular event or a left ventricular event. The term “Ap-Vs interval”, as used herein, refers to a measured intrinsic conduction time from a paced atrial (Ap) event to a sensed ventricular (Vs) event. The sensed ventricular event may be a right ventricular event or a left ventricular event.

The term “As-RVs interval” shall mean a measured intrinsic conduction time from a sensed atrial (As) event to a sensed right ventricular (RVs) event. The term “Ap-RVs interval”, as used herein, refers to a measured intrinsic conduction time from a paced atrial (Ap) event to a sensed right ventricular (RVs) event.

The term “As-LVs interval” shall mean a measured intrinsic conduction time from a sensed atrial (As) event to a sensed left ventricular (LVs) event. The term “Ap-LVs interval”, as used herein, refers to a measured intrinsic conduction time from a paced atrial (Ap) event to a sensed left ventricular (LVs) event.

The term “PR interval” shall mean an interval from onset of P-wave to start of QRS complex. In some embodiments, the PR interval can be measured during AVD search operation and can also be the intrinsic conduction time.

The terms “atrioventricular delay” and “AVD” shall mean a programmed time delay to be used by the implantable medical device in connection with delivering therapy.

The terms “AVD search operation” and “search mode” shall mean a time duration during which the system monitors for intrinsic atrial activity and intrinsic ventricular activity to determine, if possible, the intrinsic As-Vs interval or the intrinsic Ap-Vs interval.

The terms “atrioventricular delay search parameter”, “$AVD_{SEARCH}$”, and “$AVD_{SEARCH}$ duration” shall mean a time delay or interval of time to be used by the implantable medical device during the AVD search operation that is a longer interval of time compared to the AVD. The duration of the $AVD_{SEARCH}$ can be changed or adjusted as discussed herein based on one or more of heart rate, rate-responsive sensitivity(s), dynamic rate-responsive sensitivity, PR interval, conduction block, and/or non-conduction block.

The term “suspend the AVD search operation” shall mean skipping or not accomplishing the next scheduled AVD search operation and retaining the previously determined AVD. The AVD search operation can be suspended as discussed herein based on one or more interval stability characteristics, such as, but not limited to, heart rate, heart rate variability, change in posture, and/or change in activity.

The term “AVDs” shall mean an AVD in connection with delivering therapy at a ventricular site following a sensed atrial event, when an intrinsic ventricular event does not occur before AVD expires.

The term “AVDp” shall mean an AVD in connection with delivering therapy at a ventricular site following a paced atrial event, when an intrinsic ventricular event does not occur before AVD expires.

The term “activity level” shall mean types of activity currently experienced by a patient, including stationary state, rest state, exercise state, walking state, and the like.

The term “posture” shall mean postural states and/or activity levels of a patient including supine, prone, lying on a right side, lying on a left side, standing (upright), and the like.

The term “upright posture” shall mean any and all postures of the patient when the patient is in upright posture including standing or sitting. The upright posture may be identified by an accelerometer reading based on accelerometer data detected and associated with various postures.

The term “acceleration signature” shall mean signals detected by an accelerometer or other sensor associated with or of the IMD that are indicative of heart sounds generated during cardiac beats. The acceleration signatures can be analyzed for activity level and can be indicative of heart sounds generated in connection with different postures of a patient.

The term “subcutaneous” shall mean below the skin, but not intravenous. For example, a subcutaneous electrode/lead does not include an electrode/lead located in a chamber of the heart, in a vein on the heart, or in the lateral or posterior branches of the coronary sinus.

The terms “processor,” “a processor”, “one or more processors” and “the processor” shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The terms “cardiac signals”, “cardiac activity”, “cardiac activity signal”, “cardiac activity signals”, “CA signal” and “CA signals” (collectively “CA signals”) are used interchangeably throughout and shall mean measured signals indicative of cardiac activity by a region or chamber of interest. For example, the CA signals may be indicative of impedance, electrical or mechanical activity by one or more chambers (e.g., left or right ventricle, left or right atrium) of the heart and/or by a local region within the heart (e.g., impedance, electrical or mechanical activity at the AV node, along the septal wall, within the left or right bundle branch, within the purkinje fibers). The cardiac activity may be normal/healthy or abnormal/arrhythmic. An example of CA signals includes EGM signals.

Electrical based CA signals refer to an analog or digital electrical signal recorded by two or more electrodes, where the electrical signals are indicative of cardiac activity. Heart sound (HS) based CA signals refer to signals output by a heart sound sensor such as an accelerometer, where the HS based CA signals are indicative of one or more of the S1, S2, S3 and/or S4 heart sounds. Impedance based CA signals refer to impedance measurements recorded along an impedance vector between two or more electrodes, where the impedance measurements are indicative of cardiac activity.

The term “health care system” shall mean a system that includes equipment for measuring health parameters, and communication pathways from the equipment to secondary devices. The secondary devices may be at the same location as the equipment, or remote from the equipment at a different location. The communication pathways may be wired, wireless, over the air, cellular, in the cloud, etc. In one example, the healthcare system provided may be one of the systems described in U.S. Published Application 20210020294A1 entitled METHODS DEVICE AND SYSTEMS FOR HOLISTIC INTEGRATED HEALTHCARE PATIENT MANAGEMENT, filed Jul. 16, 2020, the entire contents of which are incorporated in full by reference herein. Other patents that describe example monitoring systems include U.S. Pat. No. 6,572,557; entitled SYSTEM AND METHOD FOR MONITORING PROGRESSION OF CARDIAC DISEASE STATE USING PHYSIOLOGIC SENSORS, filed Dec. 21, 2000, to Tchou et al.; U.S. Pat. No. 6,480,733 entitled METHOD FORMONITORING HEART FAILURE filed Dec. 17, 1999, to Turcott; U.S. Pat. No. 7,272,443 entitled SYSTEM AND METHOD FOR PREDICTING A HEART CONDITION BASED ON IMPEDANCE VALUES USING AN IMPLANTABLE MEDICAL DEVICE, filed Dec. 14, 2004, to Min et al; U.S. Pat. No. 7,308,309 entitled DIAGNOSING CARDIAC HEALTH UTILIZING PARAMETER TREND ANALYSIS, filed Jan. 11, 2005, to Koh; and U.S. Pat. No. 6,645,153 entitled SYSTEM AND METHOD FOR EVALUATING RISK OF MORTALITY DUE TO CONGESTIVE HEART FAILURE USING PHYSIOLOGIC SENSORS, filed Feb. 7, 2002, to Kroll et. al., the entire contents of which are incorporated in full by reference herein.

The term "IMD" shall mean an implantable medical device. Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a subcutaneous cardioverter defibrillator, cardiac monitoring device, pacemaker, cardioverter, cardiac rhythm management device, defibrillator, neurostimulator, leadless monitoring device, leadless pacemaker, and the like. The IMD may measure electrical and/or mechanical information. For example, the IMD may include one or more structural and/or functional aspects of the device(s) described in U.S. Pat. No. 9,333,351, entitled "NEUROSTIMULATION METHOD AND SYSTEM TO TREAT APNEA" issued May 10, 2016 and U.S. Pat. No. 9,044,610, entitled "SYSTEM AND METHODS FOR PROVIDING A DISTRIBUTED VIRTUAL STIMULATION CATHODE FOR USE WITH AN IMPLANTABLE NEUROSTIMULATION SYSTEM" issued Jun. 2, 2015, which are hereby incorporated by reference. The IMD may monitor transthoracic impedance, such as implemented by the CorVue algorithm offered by St. Jude Medical. Additionally or alternatively, the IMD may include one or more structural and/or functional aspects of the device(s) described in U.S. Pat. No. 9,216,285, entitled "LEADLESS IMPLANTABLE MEDICAL DEVICE HAVING REMOVABLE AND FIXED COMPONENTS" issued Dec. 22, 2015 and U.S. Pat. No. 8,831,747, entitled "LEADLESS NEUROSTIMULATION DEVICE AND METHOD INCLUDING THE SAME" issued Sep. 9, 2014, which are hereby incorporated by reference. Additionally or alternatively, the IMD may include one or more structural and/or functional aspects of the device(s) described in U.S. Pat. No. 8,391,980, entitled "METHOD AND SYSTEM FOR IDENTIFYING A POTENTIAL LEAD FAILURE IN AN IMPLANTABLE MEDICAL DEVICE" issued Mar. 5, 2013 and U.S. Pat. No. 9,232,485, entitled "SYSTEM AND METHOD FOR SELECTIVELY COMMUNICATING WITH AN IMPLANTABLE MEDICAL DEVICE" issued Jan. 5, 2016, which are hereby incorporated by reference. Additionally or alternatively, the IMD may be a subcutaneous IMD that includes one or more structural and/or functional aspects of the device(s) described in U.S. Pat. No. 10,765,860, entitled "Subcutaneous Implantation Medical Device With Multiple Parasternal-Anterior Electrodes" issued Sep. 8, 2020; U.S. Pat. No. 10,722,704, entitled "Implantable Medical Systems And Methods Including Pulse Generators And Leads" issued Jul. 28, 2020; and U.S. Pat. No. 11,045,643, entitled "Single Site Implantation Methods For Medical Devices Having Multiple Leads" issued Jun. 29, 2021, which are hereby incorporated by reference in their entireties. Additionally or alternatively, the IMD may be a leadless cardiac monitor (ICM) that includes one or more structural and/or functional aspects of the device(s) described in U.S. Pat. No. 9,949,660, entitled, "METHOD AND SYSTEM TO DISCRIMINATE RHYTHM PATTERNS IN CARDIAC ACTIVITY," which is expressly incorporated herein by reference in its entirety. Further, one or more combinations of IMDs may be utilized from the above incorporated patents and applications in accordance with embodiments herein. Embodiments may be implemented in connection with one or more subcutaneous implantable medical devices (S-IMDs). The IMD may represent a passive device that utilizes an external power source, an entirely mechanical plan will device, and/or an active device that includes an internal power source. The IMD may deliver some type of therapy/treatment, provide mechanical circulatory support, and/or merely monitor one or more physiologic characteristics of interest (e.g., PAP, CA signals, impedance, heart sounds).

System Overview

In accordance with embodiments herein, methods and systems are described for improving hemodynamics in patients treated with cardiac resynchronization therapy by minimizing the amount of time the AVD is prolonged or extended while measuring the patient's intrinsic conduction time (e.g., minimizing $AVD_{SEARCH}$ during the AVD search operation). Embodiments herein determine a rate-responsive AVD search operation that reduces the $AVD_{SEARCH}$ duration when the patient's HR is above a HR threshold. The HR threshold can be preset and/or programmable, such as at 90 beats-per-minute (bpm). When the patient's HR exceeds the HR threshold, the baseline value of $AVD_{SEARCH}$ is reduced in a rate dependent manner, such as by a predetermined time duration per bpm greater than the HR threshold. The time duration per bpm can be programmable, such as to increase or decrease the rate-response sensitivity.

Other embodiments herein disclose a dynamic rate-response sensitivity. For example, if the PR interval cannot be measured during the $AVD_{SEARCH}$, the $AVD_{SEARCH}$ may be too short and interpreted as conduction block. The rate-response sensitivity can be reduced so that the HR has less of an effect on the reduction. Conversely, if the PR interval is consistently measured, the $AVD_{SEARCH}$ may be unnecessarily long and the rate-response sensitivity can be increased. Embodiments herein can save a PR interval associated with a HR or HR range. If the PR interval associated with a current HR plus an offset is greater than the rate-responsive $AVD_{SEARCH}$, the PR interval plus offset can be used as the $AVD_{SEARCH}$ to avoid over-reducing $AVD_{SEARCH}$ in response to increases in HR. Further embodiments herein, in response to detection of conduction block, can temporarily extend the $AVD_{SEARCH}$.

In accordance with embodiments herein, the AVD search operation can be suspended for a subsequent search cycle if one or more conditions are met. For example, the AVD search operation can be suspended if i) the HR is less than a HR threshold, ii) the heart rate variability is less than a HR variability threshold, iii) no change in posture is detected, and/or iv) no change in activity level is detected.

FIG. 1 illustrates an implantable medical device (IMD) 100 intended for subcutaneous implantation at a site near the heart 111, in accordance with embodiments herein. The IMD 100 may be a dual-chamber stimulation device, such as but not limited to an implantable cardioverter defibrillator, capable of treating both fast and slow arrhythmias with stimulation therapy, including CRT, cardioversion, pacing stimulation, suspending tachycardia detection, tachyarrhythmia therapy, and/or the like. The IMD 100 may include a housing 101 to hold the electronic/computing components. The housing 101 (which is often referred to as the "can," "case," "encasing," or "case electrode") may be programmably selected to act as the return electrode for certain stimulus modes. The housing 101 further includes a connector 109 with a plurality of terminals 200-210 (shown in FIG. 2). The embodiments herein can also be incorporated into many other implantable devices, such as a transvenous device, a subcutaneous device located in pectoral regions having one or more lead proximate or into the heart, a leadless device having one or more electrode in physical communication with heart tissue, such as within a ventricle, atrium, and the like.

The IMD 100 is shown in electrical connection with a heart 111 by way of a left atrial (LA) lead having a right lead 112 and a left atrial (LA) ring electrode 128. The IMD 100 is also in electrical connection with the heart 111 by way of a right ventricular (RV) lead 110 having, in this embodiment, a left ventricle (LV) electrode 132 (e.g., P4), an LV electrode 134 (e.g., M3), an LV electrode 136 (e.g., M2), and an LV electrode 138 (e.g., D1). The RV lead 110 is transvenously inserted into the heart 111 to place the RV coil 122 in the RV apex, and the SVC coil electrode 116. Accordingly, the RV lead 110 is capable of receiving cardiac signals and delivering stimulation in the form of pacing and shock therapy to the right ventricle 140 (also referred to as the RV chamber). The IMD 100 includes RV tip electrode 126, and a right atrium (RA) electrode 123. The RV lead 110 includes an RV tip electrode 126, an RV ring electrode 124, an RV coil electrode 122, and an SVC coil electrode 116.

The IMD 100 includes a left ventricle 142 (e.g., left chamber) pacing therapy, and is coupled to a multi-pole LV lead 114 designed for placement in various locations such as a "CS region" (e.g., venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus), the epicardial space, and/or the like.

In an embodiment, the LV lead 114 is designed to receive atrial and ventricular cardiac signals and to deliver left ventricular pacing therapy using a set of multiple LV electrodes 132, 134, 136, 138. The LV lead 114 also may deliver left atrial pacing therapy using at least an LA ring electrode 128 and shocking therapy using at least the LA ring electrode 128. In alternate embodiments, the LV lead 114 includes the LV electrodes 138, 136, 134, and 132, but does not include the LA electrode 130. The LV lead 114 may be, for example, the Quartet™ LV pacing lead developed by St. Jude Medical Inc. (headquartered in St. Paul, Minn.), which includes four pacing electrodes on the LV lead. Although three leads 110, 112, and 114 are shown in FIG. 1, fewer or additional leads with various configurations of pacing, sensing, and/or shocking electrodes may optionally be used. For example, the LV lead 114 may have more or less than four LV electrodes 132-138.

The LV electrode 132 (also referred to as P4) is shown as being the most "distal" LV electrode with reference to how far the electrode is from the right ventricle 140. The LV electrode 138 (also referred to as D1) is shown as being the most "proximal" LV electrode 132-138 to the left ventricle 142. The LV electrodes 136 and 134 are shown as being "middle" LV electrodes (also referred to as M3 and M2), between the distal and proximal LV electrodes 138 and 132, respectively. Accordingly, so as to more aptly describe their relative locations, the LV electrodes 138, 136, 134, and 132 may be referred to respectively as electrodes D1, M2, M3, and P4 (where "D" stands for "distal", "M" stands for "middle", and "P" stands from "proximal", and the electrodes are arranged from most distal to most proximal, as shown in FIG. 1). Optionally, more or fewer LV electrodes may be provided on the lead 114 than the four LV electrodes D1, M2, M3, and P4.

The LV electrodes 132-138 are configured such that each electrode may be utilized to deliver pacing pulses and/or sense pacing pulses (e.g., monitor the response of the LV tissue to a pacing pulse). In a pacing vector or a sensing vector, each LV electrode 132-138 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 111 or located externally to the heart 111 (e.g., on a housing/case device 101). For example, the housing/case 101 may be referred to as the housing 101 and function as an anode in unipolar pacing and/or sensing vectors. The RV coil 122 may also function as an anode in unipolar pacing and/or sensing vectors. The LV electrodes 132-138 may be used to provide various different vectors. Some of the vectors are intraventricular LV vectors (e.g., vectors between two of the LV electrodes 132-138), while other vectors are interventricular vectors (e.g., vectors between an LV electrode 132-138 and the RV coil 122 or another electrode remote from the left ventricle 142). Further, pacing vectors or sensing vectors can be defined between an RV electrode 120, 122, or 126 to the housing 101, RV electrode 120, 122, or 126 to LV electrode 132, 134, 136, or 138, LV electrode 132, 134, 136, or 138 to the housing 101, a leadless IMD in the RV or near LV, subcutaneous parasternal electrode to the housing 101, subcutaneous parasternal and transverse electrode to the housing 101, etc. Various exemplary bipolar sensing vectors with LV cathodes may be used for sensing using the LV electrodes D1, M2, M3, and P4 and the RV coil 122. Various other types of leads and the IMD 100 may be used with various other types of electrodes and combinations of electrodes. Utilizing an RV coil electrode as an anode is merely one example. Various other electrodes may be configured as the anode electrode.

Figure 2:
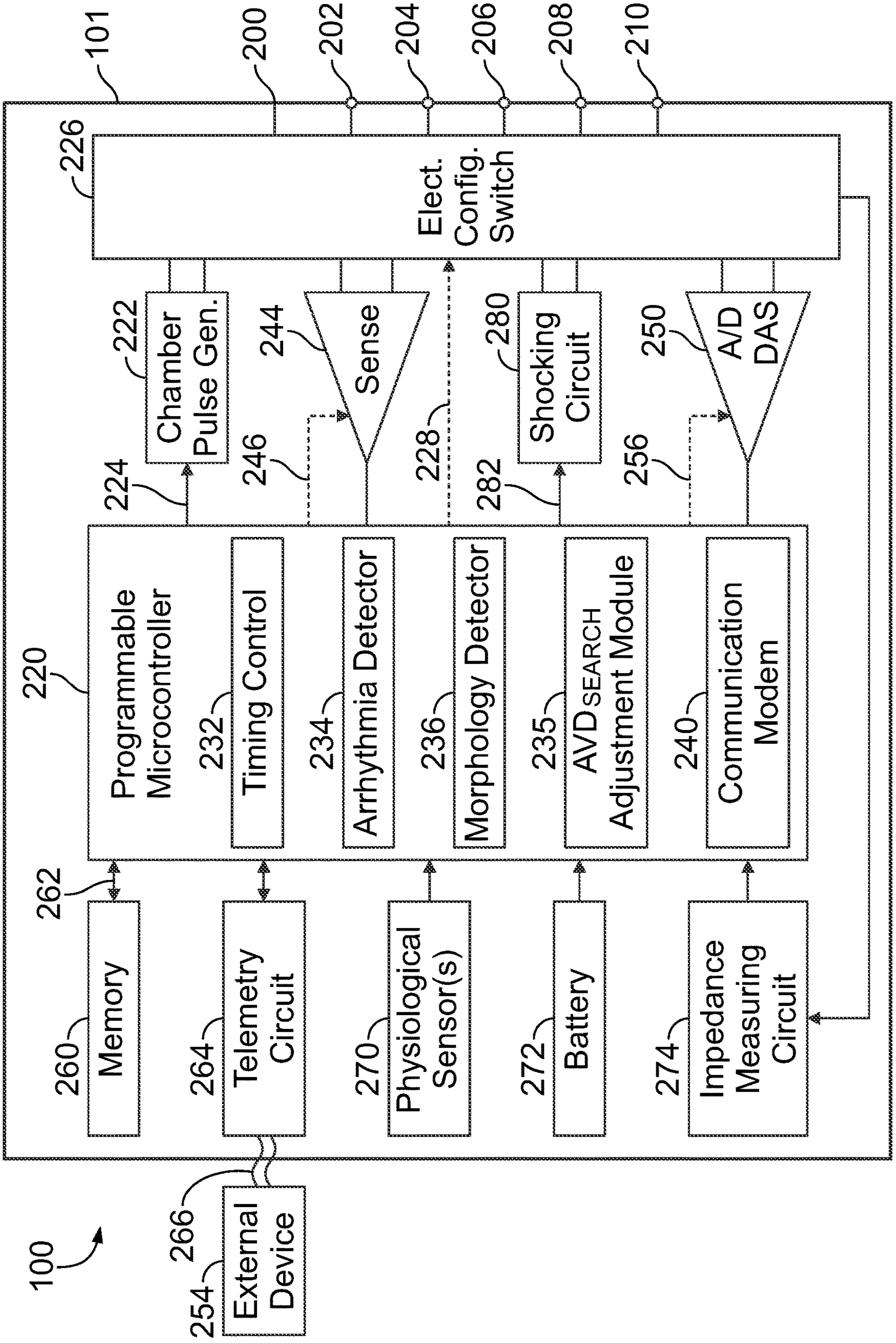
FIG. 2 illustrates a schematic view of the IMD in accordance with embodiments herein.

FIG. 2 illustrates a schematic view of the IMD 100 in accordance with embodiments herein. The IMD 100 may be a dual-chamber stimulation device, capable of treating both fast and slow arrhythmias with stimulation therapy, including CRT, cardioversion, pacing stimulation, an implantable cardioverter defibrillator, suspend tachycardia detection, tachyarrhythmia therapy, and/or the like.

The IMD 100 has a housing 101 to hold the electronic/computing components. The housing 101 (which is often referred to as the "can," "case," "encasing," or "case electrode") may be programmably selected to act as the return electrode for certain stimulus modes. The housing 101 further includes a connector (not shown) with a plurality of terminals 200-210. The terminals may be connected to electrodes that are located in various locations within and around the heart. For example, the terminals may include: a terminal 200 to be coupled to a first electrode (e.g., a tip electrode) located in a first chamber; a terminal 202 to be coupled to a second electrode located in a second chamber; a terminal 204 to be coupled to an electrode located in the first chamber; a terminal 206 to be coupled to an electrode located in the second chamber; a terminal 208 to be coupled to an electrode; and a terminal 210 to be coupled to an electrode located in the shocking circuit 280. The type and location of each electrode may vary. For example, the electrodes may include various combinations of a ring, a tip, a coil and shocking electrodes and the like.

The IMD 100 includes a programmable microcontroller 220 that controls various operations of the IMD 100, including cardiac monitoring and stimulation therapy. The microcontroller 220 includes a microprocessor (or equivalent control circuitry), one or more processors, RAM and/or ROM memory, logic and timing circuitry, state machine circuitry, and I/O circuitry. The IMD 100 further includes an atrial and/or ventricular pulse generator 222 that generates stimulation pulses for connecting the desired electrodes to the appropriate I/O circuits, thereby facilitating electrode programmability. The switch 226 is controlled by a control signal 228 from the microcontroller 220.

A pulse generator 222 is illustrated in FIG. 2. Optionally, the IMD 100 may include multiple pulse generators, similar to the pulse generator 222, where each pulse generator is coupled to one or more electrodes and controlled by the microcontroller 220 to deliver select stimulus pulse(s) to the corresponding one or more electrodes. The IMD 100 includes sensing circuits 244 selectively coupled to one or more electrodes that perform sensing operations, through the switch 226 to detect the presence of cardiac activity in the chamber of the heart 111. The output of the sensing circuits 244 is connected to the microcontroller 220 which, in turn, triggers, or inhibits the pulse generator 222 in response to the absence or presence of cardiac activity. The sensing circuits 244 receives a control signal 246 from the microcontroller 220 for purposes of controlling the gain, threshold, polarization charge removal circuitry (not shown), and the timing of any blocking circuitry (not shown) coupled to the inputs of the sensing circuits.

In the example of FIG. 2, the sensing circuit 244 is illustrated. Optionally, the IMD 100 may include multiple sensing circuits 244, similar to the sensing circuit 244, where each sensing circuit is coupled to one or more electrodes and controlled by the microcontroller 220 to sense electrical activity detected at the corresponding one or more electrodes. The sensing circuit 244 may operate in a unipolar sensing configuration or a bipolar sensing configuration.

The IMD 100 further includes an analog-to-digital (A/D) data acquisition system (DAS) 250 coupled to one or more electrodes via the switch 226 to sample cardiac signals across any pair of desired electrodes. The DAS 250 is configured to acquire intracardiac electrogram signals, convert the raw analog data into digital data and store the digital data for later processing and/or telemetric transmission to an external device 254 (e.g., a programmer, local transceiver, health care system, or a diagnostic system analyzer). The DAS 250 is controlled by a control signal 256 from the microcontroller 220.

The microcontroller 220 includes an arrhythmia detector 234 for analyzing cardiac activity signals sensed by the sensing circuit 244 and/or the DAS 250. The arrhythmia detector 234 is configured to analyze cardiac signals sensed at various sensing sites.

The microcontroller 220 further includes an $AVD_{SEARCH}$ adjustment module 235 that is configured to perform, among other things, the operations of the methods described herein. In some embodiments, the microcontroller 220 and/or $AVD_{SEARCH}$ adjustment module 235 can direct the pulse generator 222 (via control signal 224) to deliver ventricular pacing pulses based on an AVD. The $AVD_{SEARCH}$ adjustment module 235 can determine a HR, periodically initiate an AVD search operation utilizing the $AVD_{SEARCH}$, compare the HR to a threshold, and responsive to determining that the HR exceeds the threshold, reduce the $AVD_{SEARCH}$, and detect cardiac activity during the AVD search operation utilizing the reduced $AVD_{SEARCH}$. The $AVD_{SEARCH}$ is reduced by a predetermined duration for every beat per minute (bpm) that the HR exceeds the threshold, wherein the predetermined duration is stored in the memory 260. The $AVD_{SEARCH}$ adjustment module 235 is further configured to store a rate-responsive sensitivity in the memory 260, wherein the $AVD_{SEARCH}$ is reduced based on the rate-responsive sensitivity. The cardiac activity can include the Vs, wherein the $AVD_{SEARCH}$ adjustment module 235 is further configured to, in response to identifying that fewer than a select number of cardiac beats exhibit the Vs during the AVD search operation, increase the reduced $AVD_{SEARCH}$.

The $AVD_{SEARCH}$ adjustment module 235 is further configured to identify whether the cardiac activity detected during the AVD search operation is indicative of a conduction block condition or non-conduction block condition, and in response to identifying the non-conduction block condition for a consecutive predetermined number of times, reduce the reduced $AVD_{SEARCH}$. The $AVD_{SEARCH}$ adjustment module 235 is further configured to identify an intrinsic PR interval associated with the heart rate, and set the reduced $AVD_{SEARCH}$ to a greater one of i) the reduced $AVD_{SEARCH}$ and ii) the intrinsic PR interval plus a buffer length of time. The $AVD_{SEARCH}$ adjustment module 235 is further configured to set the reduced $AVD_{SEARCH}$ based on a comparison of the reduced $AVD_{SEARCH}$ and the intrinsic PR interval. The $AVD_{SEARCH}$ adjustment module 235 is further configured to identify whether the cardiac activity detected during the AVD search operation is indicative of a conduction block condition or non-conduction block condition, and in response to identifying the conduction block condition, extend the reduced $AVD_{SEARCH}$. In some cases, the $AVD_{SEARCH}$ adjustment module 235 extends the reduced $AVD_{SEARCH}$ up to a rate-dependent maximum.

In other embodiments, the microcontroller 220 and/or $AVD_{SEARCH}$ adjustment module 235 can direct the pulse generator 222 to deliver ventricular pacing pulses based on an AVD, periodically initiate an AVD search operation in which the AVD is extended, monitor one or more interval stability characteristics, and suspend the AVD search operation based on the one or more interval stability characteristics. In some cases, the interval stability characteristics include i) heart rate (HR), ii) HR variability, iii) posture, or iv) activity. A physiological sensor 270 can be configured to acquire data associated with at least one of the posture and activity. In some embodiments, the one or more interval stability characteristics is a stability characteristic of a PR interval.

In other embodiments, the interval stability characteristics include a heart rate, and the $AVD_{SEARCH}$ adjustment module 235 is configured to determine the heart rate, and compare the heart rate to a heart rate threshold stored in the memory 260, wherein the AVD search operation is suspended when the heart rate is below the heart rate threshold. In still further embodiments, the interval stability characteristics include a heart rate variability, and the $AVD_{SEARCH}$ adjustment module 235 is configured to determine the heart rate variability, and compare the heart rate variability to a heart rate variability threshold stored in the memory 260, wherein the AVD search operation is suspended when the heart rate variability is below the heart rate variability threshold.

The microcontroller 220 is operably coupled to a memory 260 by a suitable data/address bus 262. The programmable operating parameters used by the microcontroller 220 are stored in the memory 260 and used to customize the operation of the IMD 100 to suit the needs of a particular patient. The operating parameters of the IMD 100 may be non-invasively programmed into the memory 260 through a telemetry circuit 264 in telemetric communication via communication link 266 (e.g., MICS, Bluetooth low energy, and/or the like) with the external device 254. The memory 260 can store data and/or parameters used by the methods disclosed herein, such as, but not limited to, HR, one or more HR threshold, HR variability threshold, rate-responsive sensitivity, rate-responsive sensitivity parameter, baseline $AVD_{SEARCH}$ parameter, predetermined duration(s) that $AVD_{SEARCH}$ and/or PR interval are reduced or extended by, etc. The data and/or parameters may be programmable.

The IMD 100 can further include one or more physiological sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. While shown as being included within the IMD 100, the physiological sensor(s) 270 may be external to the IMD 100, and may be implanted within, worn by, in communication with a patient's skin, and/or carried by the patient. Examples of physiological sensors might include sensors that, for example, sense respiration rate, pH of blood, ventricular gradient, activity, position/posture, minute ventilation (MV), HR, and/or the like.

In some embodiments, the physiological sensor 270 can be an accelerometer. For example, the accelerometer may be a chip for placement in the IMD 100. In another embodiment, the accelerometer is formed and operates in the manner described in U.S. Pat. No. 6,937,900, entitled "AC/DC Multi-Axis Accelerometer For Determining A Patient Activity And Body Position," the complete subject matter which is expressly incorporated herein by reference. While shown as being included within the housing 101, the physiological sensor 270 may be external to the housing 101, and may be implanted within, worn by, in communication with a patient's skin, and/or carried by the patient and configured to communicate data to the IMD 100.

The IMD 100 may also include one or more processors for implementing algorithms that use accelerometer data. In one example, a diagnosis algorithm can be provided for detecting arrythmias, syncope, fainting, falls, strokes, heart attacks, or the like. In one example, the diagnosis algorithm is the diagnosis algorithm described and disclosed in U.S. published application U.S. 20210345935A1, entitled "System For Verifying A Pathologic Episode Using An Accelerometer" filed Mar. 5, 2021, that is incorporated in full by reference herein.

In one example, the IMD 100 includes a three-dimensional (3D) accelerometer-based posture algorithm that calculates parameters including extent of right (ETR) and extent of supine (ETS). The final posture of the patient can then be predicted, or identified, based on the values of ETR and ETS. The ETR provides the degree of the device tilting or flipping either to the left or right across the long axis. The expected ETR value should be close to zero when subjects have a standing posture. In some embodiments the posture algorithm can be activated at certain time(s). By not continuously obtaining and calculating acceleration data to determine the posture, battery life of the IMD 102 is saved. In one example, the posture algorithm can be the posture algorithm described and disclosed in U.S. Published Application 2023/0346258 filed Mar. 30, 2023, entitled "System For Determining Change in Position of an Implanted Medical Device Within an Implant Pocket" that is incorporated in full by reference herein.

A battery 272 provides operating power to all of the components in the IMD 100. The battery 272 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the IMD 100 employs lithium/silver vanadium oxide batteries.

The IMD 100 further includes an impedance measuring circuit 274, which can be used for many things, including sensing respiration phase. The impedance measuring circuit 274 is coupled to the switch 226 so that any desired electrode and/or terminal may be used to measure impedance in connection with monitoring respiration phase.

The microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 11 to 40 joules), as controlled by the microcontroller 220. Such shocking pulses are applied to the patient's heart through shocking electrodes. It may be noted that the shock therapy circuitry is optional and may not be implemented in the IMD 100.

The switch 226 includes a plurality of switches for connecting the desired electrodes to the appropriate I/O circuits, thereby providing complete electrode programmability. Accordingly, the switch 226, in response to a control signal 228 from the microcontroller 220, determines the polarity of the stimulation pulses (e.g., unipolar, bipolar, etc.) by selectively closing the appropriate combination of switches (not shown) as is known in the art.

The microcontroller 220 is illustrated to include timing control 232 to control the timing of the stimulation pulses (e.g., pacing rate, atrioventricular (AV) delay, atrial interconduction (A-A) delay, or ventricular interconduction (V-V) delay, etc.). The AV delay is managed to provide a fusion AV delay to fuse timing of pacing pulses with intrinsic wave fronts. The timing control 232 may also be used for the timing of refractory periods, blanking intervals, noise detection windows, evoked response windows, alert intervals, marker channel timing, and so on.

Microcontroller 220 also has a morphology detector 236 to review and analyze one or more features of the morphology of cardiac signals. Although not shown, the microcontroller 220 may further include other dedicated circuitry and/or firmware/software components that assist in monitoring various conditions of the patient's heart and managing pacing therapies.

The IMD 100 is further equipped with a communication modem (modulator/demodulator) 240 to enable wireless communication with other devices, implanted devices and/or external devices. In one implementation, the communication modem 240 may use high-frequency modulation of a signal transmitted between a pair of electrodes. As one example, the signals may be transmitted in a high-frequency range of approximately 10-80 kHz, as such signals travel through the body tissue and fluids without stimulating the heart or being felt by the patient.

Figure 3:
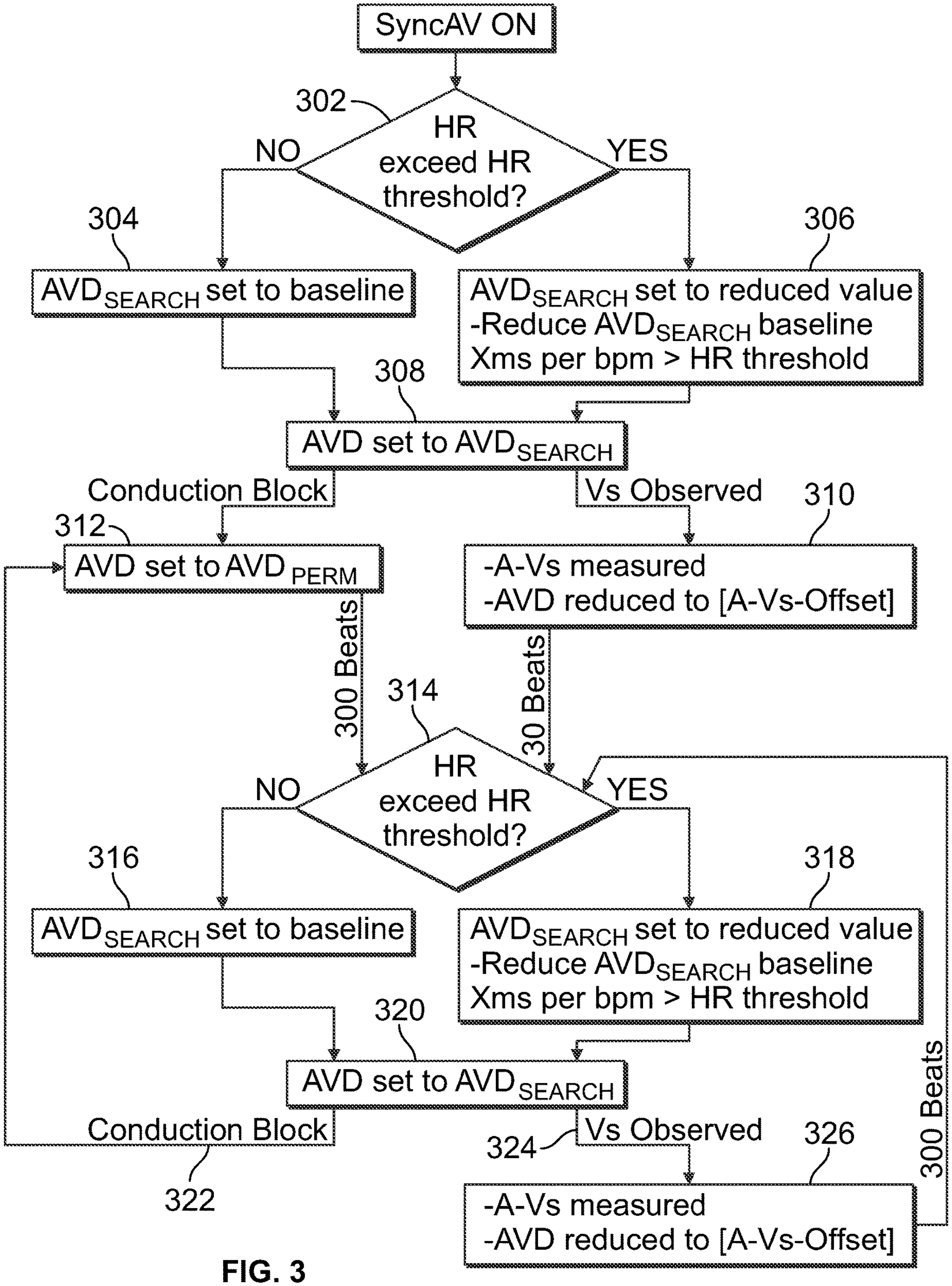
FIG. 3 illustrates a process for determining a length of time for the $AVD_{SEARCH}$ that is heart rate (HR) dependent, thus reducing the $AVD_{SEARCH}$ value from its baseline value during elevated HRs, in accordance with embodiments herein.

FIG. 3 illustrates a process for determining a length of time for the $AVD_{SEARCH}$ that is HR dependent, thus reducing the $AVD_{SEARCH}$ value from its baseline value during elevated HRs, in accordance with embodiments herein. In one example, the process of FIG. 3 is performed utilizing the HR signals detected and retrieved by the systems and methods described and incorporated herein. The operations of FIG. 3 may be implemented by hardware, firmware, circuitry and/or one or more processors housed partially and/or entirely within the IMD 100, a local external device, remote server or more generally within a health care system. Optionally, the operations of FIG. 3 may be partially implemented by an IMD 100 and partially implemented by a local external device, remote server or more generally within a health care system. For example, the IMD 100 includes IMD memory and one or more IMD processors, while each of the external devices/systems (e.g., local, remote or anywhere within the health care system) include external device memory and one or more external device processors. It should be recognized that while the operations of FIG. 3 are described in a somewhat serial manner, one or more of the operations may be continuous and/or performed in parallel with one another. For example, the various operations of the IMD 100 may be continuous and/or performed in parallel with one another and/or other functions of the IMD 100.

The process for reducing, based on HR, the length of time the AV delay is prolonged or extended during the AVD search operation is described within an overall process for implementing the AV synchronization. An advantage of reducing the $AVD_{SEARCH}$ by using the HR-responsive processes discussed herein is that the negative impact of sub-optimal AV timing (e.g., suboptimal filling of the ventricles, suboptimal blood ejection from the heart, etc.) is minimized.

The amount of extension of AV delay (e.g., $AVD_{SEARCH}$) is minimized based on HR to minimize the amount of time spent in a suboptimal pacing condition, while still determining the intrinsic PR interval. For example, the $AVD_{SEARCH}$ value can be limited to the minimum necessary to allow a ventricular sensed event to be observed and the intrinsic PR to be measured. The PR interval itself is rate dependent: faster heart rates are typically associated with shorter PR intervals. Therefore, the search delay (e.g., $AVD_{SEARCH}$) can be shorter when a faster heart rate is detected.

At 302, when the AV synchronization (SyncAV) process/protocol is activated, the one or more processors determine whether the HR exceeds an HR threshold. In some embodiments, the one or more processors can also determine the HR, or alternatively, the HR may be determined by other processes and may be stored in the memory 260. In some embodiments, the HR threshold may be 90 bpm, and optionally can be programmable and thus defined and saved by a practitioner.

If the HR is below or does not exceed the HR threshold, flow passes to 304 and the one or more processors set the $AVD_{SEARCH}$ to a baseline value. For example, for heart rates at or below 90 bpm, $AVD_{SEARCH}$ would remain or be set at its baseline value (e.g., 350 ms paced AVD (e.g., AVDp), 325 ms sensed AVD (e.g., AVDs), etc.)

Returning to 302, if the HR exceeds the HR threshold, flow passes to 306 and the one or more processors set the $AVD_{SEARCH}$ to a value that is reduced in comparison with the baseline value. In some embodiments, the reduced $AVD_{SEARCH}$ is based on the baseline values and the measured HR. The $AVD_{SEARCH}$ can be reduced in a linear and/or rate-dependent manner (e.g., reduce by X ms per bpm greater than the HR threshold). For example, the $AVD_{SEARCH}$ can be reduced by 1, 2, or 3 ms per bpm greater than 90 bpm. It should be understood that other values, including fractional values, can be used to reduce the $AVD_{SEARCH}$ in a rate-dependent manner. By way of example only, if the HR is 120 bpm at 302 and the $AVD_{SEARCH}$ is to be reduced by 2 ms for every bpm that exceeds the HR threshold of 90 bpm, the $AVD_{SEARCH}$ reduction can be determined by: 2 ms×[120 bpm−90 bpm]=60 ms. The $AVD_{SEARCH}$ baseline values are then reduced (e.g., 350−60=290 ms paced AVD, 325−60=265 ms sensed AVD, etc.).

At 308, the one or more processors enter a search mode (e.g., AVD search operation), in which the processors set the AVDp and AVDs values to equal corresponding AV search delays (collectively referred to as $AVD_{SEARCH}$) as determined in either 304 or 306 (e.g., reduced $AVD_{SEARCH}$). As discussed above, the AV search delays are set to be sufficiently long to wait for an intrinsic RV event that may be delayed following a paced atrial or sensed atrial event, but are not too long in order to avoid delaying pacing when a patient should otherwise be paced.

The processors may remain in the AVD search operation for a predetermined number of beats (e.g., 5 beats, 10 beats) and/or a predetermined period of time (e.g., 10 seconds). Additionally or alternatively, the processors may remain in the AVD search operation until a condition is satisfied, such as detecting a particular physiologic pattern (e.g., detecting 3 consecutive Vs events). While in the AVD search operation, the processors track the cardiac activity.

When the AVD search operation or search mode is terminated, the one or more processors determine whether the tracked cardiac activity is indicative of conduction block or whether a sufficient number of Vs events were detected. For example, when all or a select number of the beats, during the search mode, exhibit Vs events that are detected before the $AVD_{SEARCH}$ time expires, the processors may declare the series of beats to exhibit a normal or non-conduction block condition, in response to which flow moves to 310. As a further example, during a series of 4-8 beats, 3 or more consecutive beats may exhibit sensed ventricular Vs events before the $AVD_{SEARCH}$ time expires, in which case the processors declare the series of events to be normal.

When flow advances to 310, the one or more processors measure one or more AV intervals (e.g., intrinsic PR interval, measured intrinsic conduction time, etc.) and set the AVD based on the measured AV interval. For example, the measured AV interval can be reduced by an offset, various AV delay adjustment processes, or calculated based on other factors as known in the art. In some cases, the As-Vs interval and Ap-Vs interval used to define the AVDs and AVDp values may be determined from a select end or intermediate one of the beats measured during the search mode, such as the third or fourth event/beat in order to allow for the AV interval to stabilize following the change to the $AVD_{SEARCH}$ time. Optionally, the As-Vs interval and Ap-Vs interval may be calculated as an average (or other mathematical combination) of multiple As-Vs intervals and Ap-Vs intervals, respectively, for a desired number of multiple beats. Optionally, the AVDs and AVDp may be set at 310 in various manners, based upon the nature of the events that occur during the search mode.

The AVDp and AVDs values set at 310 are maintained for a select first number of cardiac beats (e.g., 20-40 beats) associated with a normal or non-conduction block condition.

Returning to 308, when fewer than the select number of the beats exhibit Vs events during the AVD search operation utilizing the reduced $AVD_{SEARCH}$ (assuming the HR>HR threshold at 302), the one or more processors may declare the series of beats to exhibit an abnormal or conduction block condition. When an abnormal or conduction block condition is identified, flow moves to 312. For example, during the search mode, three consecutive Vs events do not occur. Alternatively, during the series of 4-8 beats, fewer than 3 consecutive beats may exhibit Vs events before the reduced $AVD_{SEARCH}$ time expires.

At 312, the one or more processors identify the presence of conduction block (or a similar abnormal condition), and in response thereto, revert the AVDs and AVDp delays to base programmed lengths (e.g., set $AVDp_{-base}$ equal to 100 ms to 150 ms and set $AVDs_{-base}$ equal to 125 ms to 175 ms, etc.). The base $AVDp_{-base}$ and $AVDs_{-base}$ lengths are maintained for a select second number of cardiac beats (e.g., 200-300 beats).

The AVDp and AVDs values set at 310 or 312 are utilized by the IMD 100 for corresponding numbers of cardiac beats (e.g., 20-40 or 200-300), and thereafter flow continues to 314. At 314, similar to 302, the one or more processors determine whether the HR exceeds the HR threshold. In some embodiments, the one or more processors can also determine the HR just prior to 314, or alternatively, the HR may be determined by other processes and stored in the memory 260, and thus may have changed since the HR was identified at 302.

If the HR does not exceed the HR threshold, flow passes to 316 and the one or more processors set the $AVD_{SEARCH}$ to the baseline values as discussed above in 304. If the HR exceeds the HR threshold, flow passes to 318 and the one or more processors set the $AVD_{SEARCH}$ to a value that is reduced in comparison with the baseline value, as discussed above in 306.

Flow passes to 320 where, after the corresponding number of select cardiac beats, the one or more processors enter the AVD search operation and reset the AVDp and AVDs values to the corresponding $AVD_{SEARCH}$ values, thereby reentering a search mode. The AV search delays set at 320 may be the same as or differ from the AV search delays set at 308. The duration of the search mode at 320 may be the same as or different from the duration of the search mode at 308. For example, the processors may maintain the search mode at 320 for 5 or more beats. In some embodiments, the one or more processors determine whether a select number of consecutive sensed ventricular Vs events occur and based thereon, flow branches along 322 or 324. For example, when three or more consecutive Vs events are detected during the search mode, flow branches along 324.

At 326, the one or more processors measure one or more AV intervals (e.g., PR intervals, measured intrinsic conduction time, etc.) and set the AVDp and AVDs based on the measured AV intervals, defined and/or calculated offsets, and the like. As explained above in connection with 310, at 326, the As-Vs interval and Ap-Vs interval, used to define the AVDs and AVDp values, may be determined from a select one of the beats measured during the search mode or calculated as an average (or other mathematical combination) of multiple As-Vs intervals and Ap-Vs intervals. Flow can then pass to 314.

Returning to 320, when the one or more processors determine that fewer than the select number of consecutive sensed ventricular Vs events occur, the processors determine that the patient exhibited a conduction block condition and in response thereto, flow branches along 322 and returns to 312. For example, the processors may identify a conduction block condition when the processors do not detect three or another select number of consecutive sensed ventricular Vs events during the search mode. As noted above, at 312, the AVDp and AVDs values revert to the base programmed lengths for a longer select number of beats, such as $300\times2^N$ beats before reentering the search mode again. In some cases, the variable N equals the number of consecutive searches in which conduction block was identified.

Additionally or alternatively, anytime the select number of consecutive sensed ventricular Vs events occur while the AVDp and AVDs values are already reduced (e.g., within either a 30- or 300-beat window), both AVDp and AVDs values can be further reduced, such as for another 30 beats before re-entering the search mode. Additionally or alternatively, whenever the processors determine that it is desirable to further reduce the AVDp and AVDs values, after already being reduced, the processors may first enter the search mode for a shortened search window (e.g., after 30 beats instead of 300 beats) to allow the processors to perform a fast AV interval assessment.

In some embodiments, the rate-responsive sensitivity of the $AVD_{SEARCH}$ can be programmable. For example, one or more rate-responsive sensitivity parameters (e.g., level, specific length of time, etc.) can be saved in memory 260. By way of example only, different levels of rate-responsive sensitivity can be identified and have an associated length of time (e.g., Low: 1 ms per bpm>90, Medium: 2 ms per bpm>90, High: 3 ms per bpm>90).

In other embodiments, a QRS duration can be measured, such as at 310, 326, and compared to a threshold (e.g., time duration, variation, etc.) to determine whether the $AVD_{SEARCH}$ value should be shortened or extended. In some embodiments, a number or percentage of fused beats can be compared to threshold(s) to determine whether the $AVD_{SEARCH}$ value should be shortened or extended. For example, an estimation of QRS-based or morphology-based evaluation of fusion could be used to determine whether the $AVD_{SEARCH}$ value should be adjusted.

Accordingly, the IMD 100 delivers a particular treatment for the medical condition of heart failure. The treatment of heart failure includes adjusting the duration of $AVD_{SEARCH}$ that is used during the AVD search operation to more closely match the patient's instant HR. By reducing the $AVD_{SEARCH}$ when the patient's HR is elevated, the IMD 100 initiates ventricular pacing pulses, if needed, during a time duration that is closer to the patient's current HR rather than the longer default $AVD_{SEARCH}$ duration. Reducing the $AVD_{SEARCH}$, while still also evaluating the patient to ensure that adequate cardiac activity is sensed during the AVD search operation, improves upon the previously experienced suboptimal filling of the ventricles and suboptimal blood ejection from the heart experienced when the patient has an elevated HR and the $AVD_{SEARCH}$ is set to a default value.

Figure 4:
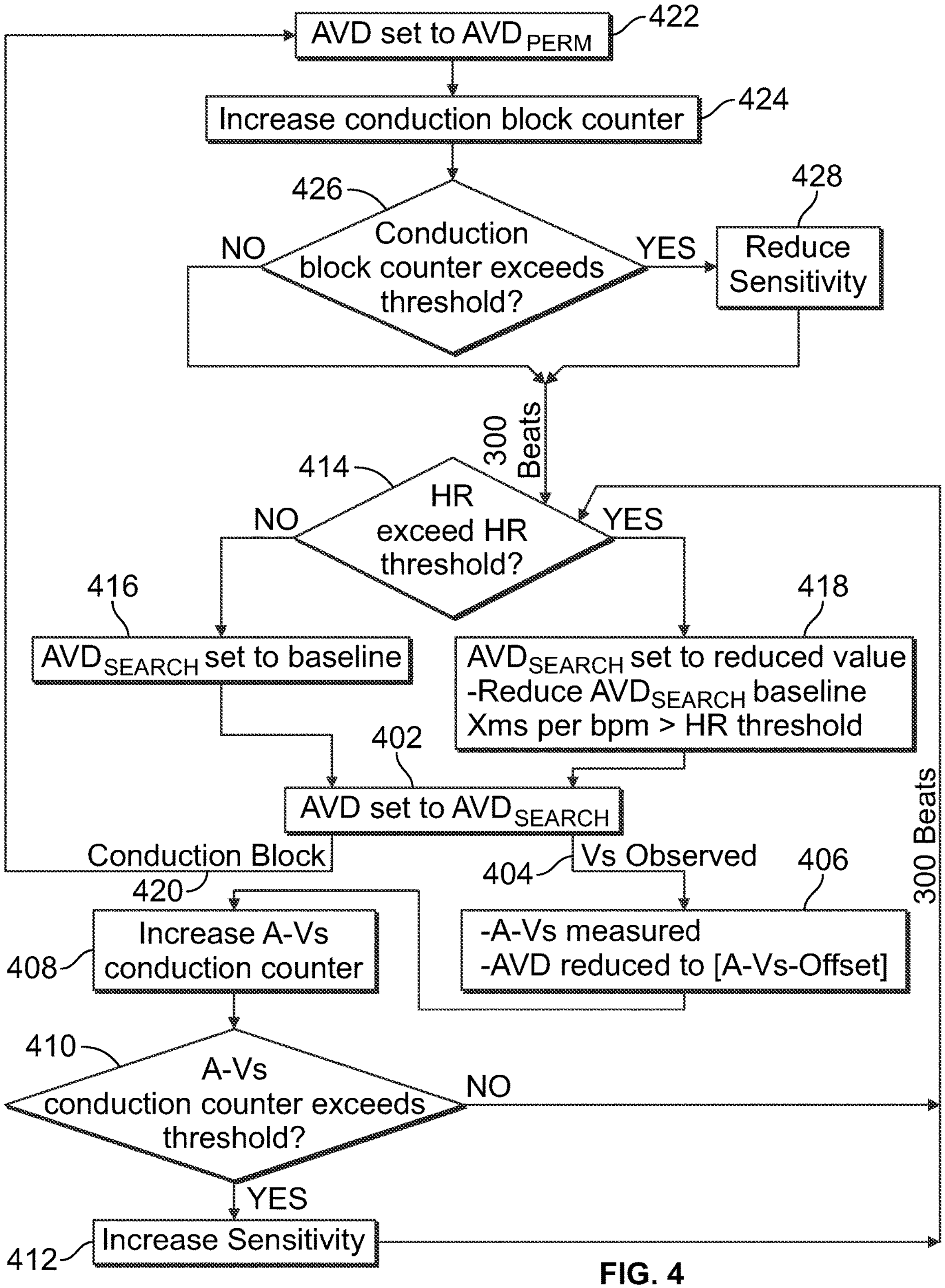
FIG. 4 illustrates a process for dynamically adjusting the rate-responsive sensitivity in accordance with embodiments herein.

FIG. 4 illustrates a process for dynamically adjusting the rate-responsive sensitivity in accordance with embodiments herein. In one example, the process of FIG. 4 is performed utilizing the HR signals detected and retrieved by the systems and methods described herein. The operations of FIG. 4 may be implemented by hardware, firmware, circuitry and/or one or more processors housed partially and/or entirely within the IMD 100, a local external device, remote server or more generally within a health care system. Optionally, the operations of FIG. 4 may be partially implemented by an IMD 100 and partially implemented by a local external device, remote server or more generally within a health care system. It should be recognized that while the operations of FIG. 4 are described in a somewhat serial manner, one or more of the operations may be continuous and/or performed in parallel with one another. For example, the various operations of the IMD 100 may be continuous and/or performed in parallel with one another and/or other functions of the IMD 100.

If sufficient ventricular sensed events are not observed with the rate-responsive $AVD_{SEARCH}$ values, and thus the PR interval cannot be measured, then the rate-responsive sensitivity can be reduced. In some cases, the $AVD_{SEARCH}$ is not long enough to allow intrinsic AV conduction and the $AVD_{SEARCH}$ is too responsive to the elevated HR. Accordingly, the sensitivity can be reduced, such as after conduction block is detected consecutively for a predefined number of times. In contrast, if the PR interval can be consistently measured (e.g., conduction block has not been observed consecutively for a predefined number of times), the sensitivity can be increased.

For simplicity, the process of FIG. 4 will be discussed in relation to FIG. 3, and like item numbers will be referenced. For example, at 402 (e.g., 320), the one or more processors enter the AVD search operation as discussed above, in which the processors set the AVDp and AVDs values to equal corresponding AV search delays as determined in either 416/316 (e.g., $AVD_{SEARCH}$ set to baseline) or 418/318 (e.g., $AVD_{SEARCH}$ set to reduced value). The processors may remain in the search mode (e.g., AVD search operation) for a predetermined number of beats (e.g., 5 beats, 10 beats) and/or a predetermined period of time (e.g., 10 second). Additionally or alternatively, the processors may remain in the search mode until a condition is satisfied (e.g., a particular physiologic pattern).

When the search mode is terminated at 402, the one or more processors determine whether the detected cardiac activity is indicative of conduction block or whether a sufficient number of Vs events were detected. For example, when all or a select number of the beats, during the search mode, exhibit Vs events that are detected before the $AVD_{SEARCH}$ time expires, the processors may declare the series of beats to exhibit a normal or non-conduction block condition at 404, in response to which flow moves to 406 (e.g., 326). As a further example, during a series of 4-8 beats, 3 or more consecutive beats may exhibit sensed ventricular Vs events before the $AVD_{SEARCH}$ time expires, in which case the processors declare the series of events to be normal.

When flow advances to 406, the one or more processors measure one or more AV intervals and set the AVDs based on the measured AV interval.

At 408, the one or more processors update an A-Vs conduction counter. The A-Vs conduction counter can be incremented to record the number of times non-conduction block has been observed consecutively. In some embodiments, when the A-Vs conduction counter is increased, the one or more processors can reset a corresponding conduction block counter to zero (discussed further below).

At 410, the one or more processors determine whether the A-Vs conduction counter exceeds a threshold. The threshold can be a default value or a programmed value and may be dependent upon the physiological needs of the patient. If the threshold is exceeded, the A-Vs conduction parameters have been satisfied for a minimum number of consecutively acquired cycles. In some cases, this can indicate that the sensitivity can be increased, resulting in a shorter $AVD_{SEARCH}$. In some embodiments, the minimum number of consecutively acquired cycles can be two, three, or more consecutive cycles. Flow passes to 412 and the one or more processors increase the rate-responsive sensitivity value, such as from 1 ms to 2 ms (e.g., from low to medium) or 2 ms to 3 ms (e.g., from medium to high). Flow then passes to 414 (e.g., 314).

If however, at 410, the A-Vs conduction counter is below or does not exceed the threshold, the flow passes to 414.

The one or more processors accomplish 414 (e.g., 314), 416 (e.g., 316), 418 (e.g., 318), and 402 (e.g., 320) as discussed in FIG. 3. However, if the sensitivity has been increased, the length of time (e.g., X ms) will increase from the previous adjustment.

Returning to 402, when fewer than the select number of the beats exhibit Vs events during the $AVD_{SEARCH}$, the one or more processors may declare the series of beats to exhibit an abnormal or conduction block condition. When an abnormal or conduction block condition is identified, flow moves to 420 (e.g., 322). For example, during the search mode, three consecutive Vs events do not occur. Alternatively, during the series of 4-8 beats, fewer than 3 consecutive beats may exhibit Vs events before the $AVD_{SEARCH}$ time expires.

At 422 (e.g., 312), the one or more processors identify the presence of conduction block (or a similar abnormal condition), and in response thereto, revert the AVDs and AVDp delays to baseline $AVD_{SEARCH}$ parameters as discussed above. The base AVDp-base and AVDs-base lengths are maintained for a select second number of cardiac beats (e.g., 200-300 beats).

At 424, the one or more processors increase the conduction block counter. In some embodiments, the one or more processors may reset or zero the A-Vs conduction counter. At 426, the one or more processors determine whether the conduction block counter exceeds a threshold. The conduction block counter threshold can be the same number of cycles as the A-Vs conduction counter threshold (e.g., 1, 2, 3, or more cycles) or different. When the conduction block counter threshold is exceeded, this can indicate that the $AVD_{SEARCH}$ is not long enough to allow intrinsic AV conduction, and that the AVD search is too responsive to the elevated HR.

When the conduction block counter threshold is exceeded, flow passes to 428 and the one or more processors decrease the rate-responsive sensitivity value, such as from 2 ms to 1 ms (e.g., from medium to low) or 3 ms to 2 ms (e.g., from high to medium). Flow passes to 414 (e.g., 314). In some embodiments, the conduction block counter threshold can be 1, and the sensitivity can be reduced, such as from high to medium and from medium to low.

If however, at 426, the conduction block counter is below or does not exceed the threshold, the flow passes to 414.

Figure 5:
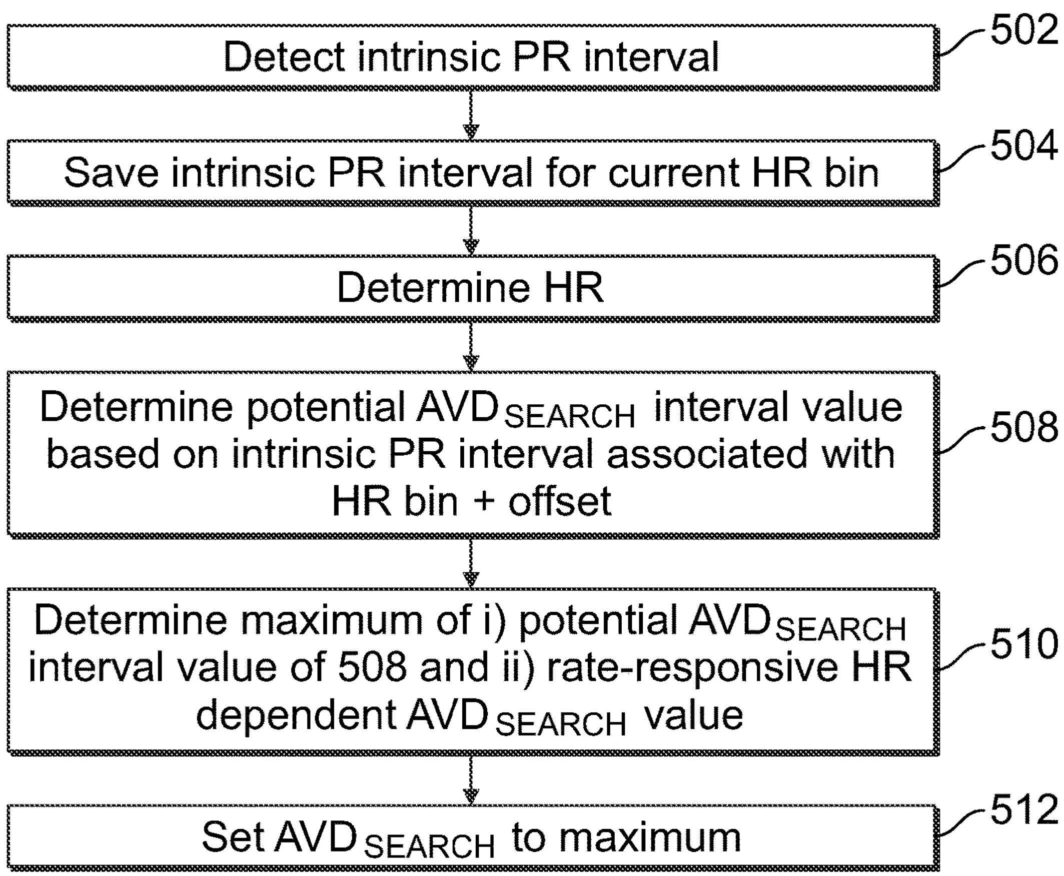
FIG. 5 illustrates a process for dynamically setting the $AVD_{SEARCH}$ based on either the rate-responsive, HR-dependent $AVD_{SEARCH}$ value or a saved PR interval to avoid over-reducing $AVD_{SEARCH}$ in response to increases in HR in accordance with embodiments herein.

FIG. 5 illustrates a process for dynamically setting the $AVD_{SEARCH}$ based on either the rate-responsive, HR-dependent $AVD_{SEARCH}$ value or a saved PR interval to avoid over-reducing $AVD_{SEARCH}$ in response to increases in HR in accordance with embodiments herein. In one example, the process of FIG. 5 is performed utilizing the HR signals detected and retrieved by the systems and methods described herein. The operations of FIG. 5 may be implemented by hardware, firmware, circuitry and/or one or more processors housed partially and/or entirely within the IMD 100, a local external device, remote server or more generally within a health care system. Optionally, the operations of FIG. 5 may be partially implemented by an IMD 100 and partially implemented by a local external device, remote server or more generally within a health care system. It should be recognized that while the operations of FIG. 5 are described in a somewhat serial manner, one or more of the operations may be continuous and/or performed in parallel with one another. For example, the various operations of the IMD 100 may be continuous and/or performed in parallel with one another and/or other functions of the IMD 100.

In the example of FIG. 5, the process of FIG. 3 for utilizing a rate-responsive, HR-dependent $AVD_{SEARCH}$ value is expanded to identify another potential $AVD_{SEARCH}$ value that may be appropriate and to avoid over-reducing the $AVD_{SEARCH}$ value in response to increases in HR. As explained hereafter, to avoid over-reducing the $AVD_{SEARCH}$, a most recent intrinsic PR interval for associated HR bins can be saved. In some embodiments, the $AVD_{SEARCH}$ can be set to the maximum of the rate-responsive, HR-dependent $AVD_{SEARCH}$ value or the saved PR interval for the appropriate HR bin, plus an offset.

At 502, the one or more processors detect the intrinsic PR interval. For example, the intrinsic PR interval may be measured at 310, 326 of FIG. 3.

At 504, the one or more processors save the intrinsic PR interval associated with the current HR bin. In some embodiments, HR bins can be established for increments of 10 bpm, such as from 40 to 180 bpm, although other increments and ranges are contemplated. For example, for an intrinsic PR interval measured when the HR is 97, the processors save the intrinsic PR interval in a HR bin for 90-100 bpm. Any previous intrinsic PR interval saved in the associated HR bin can be discarded. Therefore, as the SyncAV protocol is active, a new intrinsic PR interval is measured (e.g. at 310, 326, etc.) and stored in the associated HR bin.

At 506, the one or more processors determine the current HR. The HR can be determined by other processes as discussed herein, or by the process of one of FIG. 3 or 5.

At 508, the one or more processors retrieve the intrinsic PR interval associated with the current HR and determine an interval value by adding an offset or buffer length of time to the intrinsic PR interval. (e.g., potential $AVD_{SEARCH}$ interval=intrinsic PR interval+N ms). In some embodiments, the offset N can be 20 ms, but is not so limited.

At 510, the one or more processors determine a maximum or the longer of i) the potential $AVD_{SEARCH}$ interval value identified at 508 and ii) the rate-responsive HR dependent $AVD_{SEARCH}$ value identified at 306 or 318.

At 512, the one or more processors set the $AVD_{SEARCH}$ to the maximum value identified at 510. This provides the advantage of avoiding over-reducing the $AVD_{SEARCH}$ in response to increases in HR rate.

Figure 6:
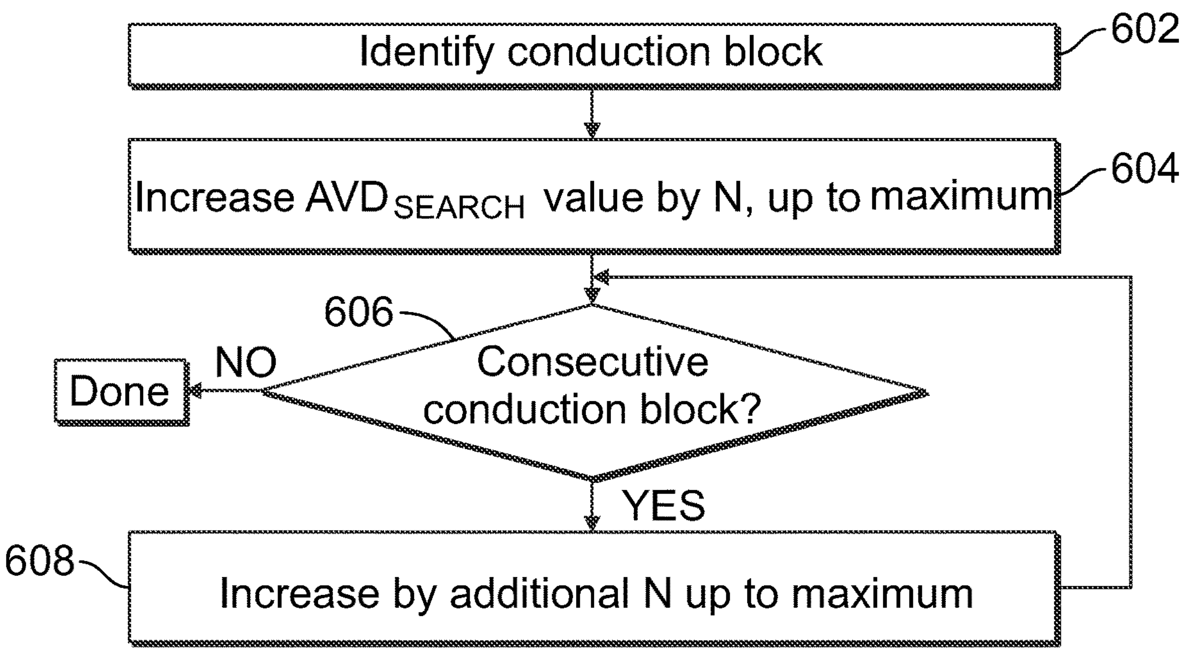
FIG. 6 illustrates a process for increasing the $AVD_{SEARCH}$ value after conduction block is identified in accordance with embodiments herein.

FIG. 6 illustrates a process for increasing the $AVD_{SEARCH}$ value after conduction block is identified in accordance with embodiments herein. In one example, the process of FIG. 6 is performed utilizing the HR signals detected and retrieved by the systems and methods described herein. The operations of FIG. 6 may be implemented by hardware, firmware, circuitry and/or one or more processors housed partially and/or entirely within the IMD 100, a local external device, remote server or more generally within a health care system. Optionally, the operations of FIG. 6 may be partially implemented by an IMD 100 and partially implemented by a local external device, remote server or more generally within a health care system. It should be recognized that while the operations of FIG. 6 are described in a somewhat serial manner, one or more of the operations may be continuous and/or performed in parallel with one another. For example, the various operations of the IMD 100 may be continuous and/or performed in parallel with one another and/or other functions of the IMD 100.

In the example of FIG. 6, the process of FIG. 3 for utilizing a rate-responsive, HR-dependent $AVD_{SEARCH}$ value is expanded to identify yet another potential $AVD_{SEARCH}$ value that may be appropriate and to avoid over-reducing the $AVD_{SEARCH}$ value in response to increases in HR. As explained hereafter, to avoid over-reducing the $AVD_{SEARCH}$ value, the rate-responsive, HR-dependent $AVD_{SEARCH}$ can be temporarily extended at the next AVD search operation following conduction block, by a predetermined value.

At 602, the one or more processors identify conduction block (e.g., at 308, 320, etc.)

At 604, the one or more processors increase the $AVD_{SEARCH}$ by N ms, such as up to a maximum. In some embodiments, the maximum can be a rate-dependent maximum. For example, the AVD identified at 318 can be increased by N ms. In some embodiments, N can be 20 ms, but is not so limited. In other embodiments, the $AVD_{SEARCH}$ value can be increased up to a maximum (e.g., to 350/325 ms paced/sensed AVD).

At 606, the one or more processors determine if conduction block is consecutively detected. If yes, flow passes to 608 where, after the next $AVD_{SEARCH}$ value is determined, such as at 318, the one or more processors increase the $AVD_{SEARCH}$ value by N ms, up to a maximum or rate-dependent maximum. In other embodiments, a greater value of N can be used, or a multiple of N.

In some embodiments, for each instance of conduction block the current $AVD_{SEARCH}$ value is extended by N ms until the maximum (e.g., 350/325 ms paced/sensed AVD), at which point the intersearch interval is doubled (e.g., from 256 to 512 beats, from 512 to 1024 beats, and so on).

Figure 7:
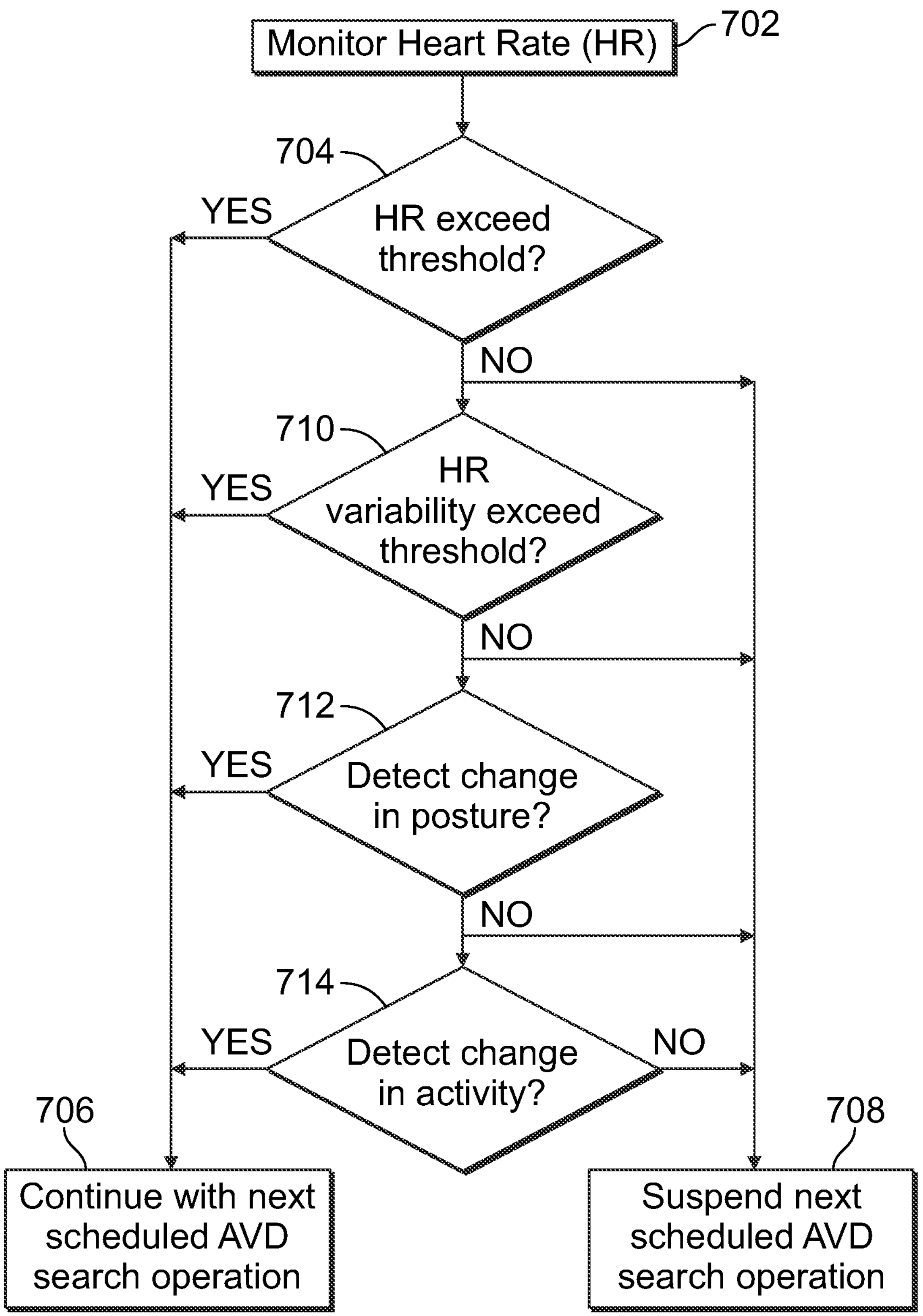
FIG. 7 illustrates a process for automatically minimizing an amount of time spent with prolonged AV delays and in some cases, suspending a periodically programmed AVD search operation in accordance with embodiments herein.

FIG. 7 illustrates a process for automatically minimizing an amount of time spent with prolonged AV delays and in some cases, suspending a periodically programmed AVD search operation in accordance with embodiments herein. In one example, the process of FIG. 7 is performed utilizing the HR signals and acceleration signatures detected and retrieved by the systems and methods described herein. The operations of FIG. 7 may be implemented by hardware, firmware, circuitry and/or one or more processors housed partially and/or entirely within the IMD 100, a local external device, remote server or more generally within a health care system. Optionally, the operations of FIG. 7 may be partially implemented by an IMD 100 and partially implemented by a local external device, remote server or more generally within a health care system. It should be recognized that while the operations of FIG. 7 are described in a somewhat serial manner, one or more of the operations may be continuous and/or performed in parallel with one another. For example, the various operations of the IMD 100 may be continuous and/or performed in parallel with one another and/or other functions of the IMD 100.

FIG. 7 can be used together with one or all of the processes of FIGS. 3-6 and employs a dynamic search interval extension mechanism. In other embodiments, the dynamic search interval extension mechanism can be used with the SyncAV algorithm/protocol that does not employ any of the rate-responsive search extensions of FIGS. 3-6.

One way to limit the negative impact of the extended AVD is to identify condition(s) wherein the extension is unnecessary and thus limit how often the SyncAV algorithm/protocol extends the AVD to the $AVD_{SEARCH}$ value. For example, the AVD search operation can be suspended (e.g., not performed) as discussed below based on one or more characteristics or conditions being met, such as HR being below or not exceeding a threshold, HR variability being below or not exceeding a threshold, no change detected in posture, and/or no change detected in activity levels. Accordingly, the $AVD_{SEARCH}$ is only used, in some embodiments, during periods of activity and/or based on certain HR conditions. Further advantages are that the dynamic search interval extension mechanism changes the interval between AVD search operations, effectively increasing the interval between the 5-beat search windows when certain condition(s) are met and changes in the intrinsic PR interval are not expected to occur, while maintaining the scheduled interval between AVD search operations during periods of elevated heart rate, activity, exercise, etc., when changes in intrinsic PR interval are expected to occur.

At 702, the one or more processors monitor the HR. For example, the HR can be monitored prior to the start of the SyncAV protocol or immediately after the SyncAV protocol is initiated.

At 704, the one or more processors compare the current HR to a threshold HR. The threshold HR can be stored in the memory 260 and can be programmable. Therefore, the HR threshold can be customized to the patient's physiological need. In some embodiments, the threshold HR can be 90 bpm. If the current HR exceeds the threshold HR, flow passes to 706 and the one or more processors continue with the next scheduled AVD search operation.

If the current HR is below or does not exceed the threshold HR, the patient may be at rest or asleep, and flow can pass to 708 and the one or more processors suspend the next scheduled AVD search operation. For example, the dynamic search interval extension mechanism has determined that there is no reason to conduct a new search for an updated PR interval at this time. Therefore, the current AVD is retained. For example, the current AVDp and AVDs values are maintained for a select number of cardiac beats (e.g., 200-300 beats).

Alternatively, more than one stability characteristic can be determined relative to a threshold or parameter before suspending the next scheduled AVD search operation. For example, any two or more of the stability characteristics discussed herein may be required to suspend the AVD search operation to avoid a conclusion that may be false based on result of only one condition, only two conditions, etc. Therefore, it should be understood that some or all of the conditions of 704, 710, 712, and 714 may be accomplished simultaneously.

Returning to 704, if the current HR is below or does not exceed the threshold HR, flow can pass to 710 and the one or more processors determine whether the HR variability exceeds a HR variability threshold. The patient's HR may be more variable during periods of activity and/or exercise. The HR variability threshold can be stored in the memory 260 and can be programmable. Although not so limited, the HR variability threshold can be standard deviation as a percent of mean, and in some embodiments may be calculated between the last scheduled or conducted AVD search operation and the next scheduled AVD search operation. Alternatively, the HR variability threshold can be calculated over a fixed and/or programmable period of time, fixed and/or programmable number of heart cycles, etc. If the HR variability exceeds the HR variability threshold, flow passes to 706 and the one or more processors continue with the next scheduled AVD search operation. If the HR variability is below or does not exceed the HR variability threshold, flow passes to either 708 or 712. In other embodiments, at 710 the one or more processors can determine a stability characteristic of the PR interval or other measurement of stability of intrinsic conduction.

At 712, the one or more processors determine whether there has been a change detected in posture, such as by accelerometer readings associated with the physiological sensor(s) 270. For example, if no change has been detected in posture, the patient may be asleep or resting. If change is detected in posture, flow passes to 706 and the one or more processors continue with the next scheduled AVD search operation. If no change is detected, flow passes to 708 or 714.

At 714, the one or more processors determine whether there has been a change detected in activity level, such as by accelerometer readings associated with the physiological sensor(s) 270. Similarly, if no change has been detected in activity, the patient may be asleep or resting. If change is detected in activity level, flow passes to 706 and the one or more processors continue with the next scheduled AVD search operation. If no change is detected, flow passes to 708.

The embodiment of FIG. 7 enables the one or more processors to minimize the number of times the AVD search operation is accomplished, and thus minimize the number of times the patient experiences a potentially longer than desirable AV delay. Several interval stability characteristics are monitored to determine whether the patient is in a physiological state that allows maintaining the current AV delay.

Accordingly, the IMD 100 delivers a particular treatment for the medical condition of heart failure. The treatment of heart failure includes suspending the AVD search operation during times of rest and/or inactivity of the patient. During periods such as these, the patient's PR interval will remain stable. The IMD 100 monitors one or more conditions associated with cardiac stability, such as HR, HR variability, posture, and/or activity. If the monitored condition(s) is below or does not exceed a threshold, the next scheduled AVD search operation is suspended. This provides the advantage of applying a consistent AVD during the patient's pacing therapy, without unnecessarily extending the $AVD_{SEARCH}$ to a value that can result in the previously experienced suboptimal filling of the ventricles and suboptimal blood ejection from the heart.

Although the Figures included herein illustrate an implantable dual-chamber stimulation device capable of CRT, the features, methods, and/or processes described herein, including but not limited to SyncAV-based fusion pacing with minimized search extensions, can be used in a plurality of therapies and by any implantable and/or external device, including but not limit to those described and/or incorporated by reference herein. For example, the methods/processes can be used to fuse intrinsic features with left bundle branch area pacing (LBBAP) therapy for bradycardia and/or for left ventricle (LV) dysfunction (e.g., low ejection fraction percentage) disease states. Additionally or alternatively, low voltage or high voltage dual chamber devices (e.g. without LV lead) can be used.

Embodiments may be implemented in connection with the methods and systems described in U.S. Application Ser. No. 63/353,647, entitled "METHODS AND SYSTEMS FOR POSTURE DEPENDENT IMPLANTABLE CARDIOVERTER DEFIBRILLATOR THERAPY" filed Jun. 20, 2022; U.S. Pat. No. 11,273,312, entitled "Method and system for dynamic device-based delay adjustment" having an issue date of Mar. 15, 2022; U.S. Pat. No. 7,643,878, entitled "System and method for determining atrioventricular pacing delay based on atrial depolarization" having an issue date of Jan. 5, 2010; U.S. Pat. No. 6,832,112, entitled "Method of adjusting an AV and/or PV delay to improve hemodynamics and corresponding implantable stimulation device" having an issue date of Dec. 14, 2004; U.S. Pat. No. 7,941,217, entitled "Techniques for promoting biventricular synchrony and stimulation device efficiency using intentional fusion" having an issue date of May 10, 2011; U.S. Pat. No. 7,778,706, entitled "Rate adaptive biventricular and cardiac resynchronization therapy" having an issue date of Aug. 17, 2010; U.S. Pat. No. 7,702,390, entitled "Rate adaptive biventricular and cardiac resynchronization therapy" having an issue date of Apr. 20, 2010; U.S. Pat. No. 11,154,719, entitled "Method and system utilizing a percentage-based atrio-ventricular delay adjustment" having an issue date of Oct. 26, 2021; U.S. Pat. No. 5,741,308, entitled "Dual-chamber implantable pacemaker and method of operating same for automatically setting the pacemaker's AV interval as a function of a natural measured conduction time" having an issue date of Apr. 21, 1998; U.S. Pat. No. 8,442,634, entitled "Systems and methods for controlling ventricular pacing in patients with long inter-atrial conduction delays" having an issue date of May 14, 2013; U.S. Pat. No. 11,311,733, entitled "Method and system for adaptive bi-ventricular fusion pacing" having an issue date of Apr. 26, 2022; U.S. Pat. No. 10,589,100, entitled "Method and device for pacing latency based multi-point pacing" having an issue date of Mar. 17, 2020; U.S. Pat. No. 10,668,289, entitled "Method and device for controlling rate adaptive pacing based on heart sounds" having an issue date of Jun. 2, 2020; U.S. Pat. No. 11,400,297, entitled "Method and device for managing pacing therapy based on interventricular septal activity" having an issue date of Aug. 2, 2022; U.S. Pat. No. 10,967,189, entitled "Methods and systems for selectively delivering different types of bi-ventricular pacing" having an issue date of Apr. 6, 2021; U.S. Pat. No. 11,311,733, entitled "Method and system for adaptive bi-ventricular fusion pacing" having an issue date of Apr. 26, 2022; U.S. Pat. No. 10,173,066, entitled "Methods and systems for selectively delivering different types of bi-ventricular pacing" having an issue date of Jan. 8, 2019; U.S. Pat. No. 10,582,874, entitled "Method and device for electrogram based estimation of QRS duration" having an issue date of Mar. 10, 2020; U.S. Pat. No. 10,569,091, entitled "Method and device for discrimination of left ventricular pseudo-fusion pacing" having an issue date of Feb. 25, 2020; which are hereby incorporated by reference in their entireties.

Embodiments may be implemented in connection with one or more implantable medical devices (IMDs). Non-limiting examples of IMDs include one or more of implantable leadless monitoring and/or therapy devices, and/or alternative implantable medical devices. For example, the IMD may represent a cardioverter defibrillator, pacemaker, cardioverter, cardiac rhythm management device, defibrillator, leadless pacemaker and the like. For example, leadless implantable medical device (LIMD) can include one or more structural and/or functional aspects of the device(s) described in U.S. Pat. No. 9,216,285 "Leadless Implantable Medical Device Having Removable And Fixed Components" which is hereby incorporated by reference in its entirety. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference in their entireties.

Additionally or alternatively, the IMD may be a subcutaneous IMD as discussed herein. Further, one or more combinations of IMDs may be utilized from the incorporated patents and applications in accordance with embodiments herein.

In some embodiments, the physiologic sensor may be implemented as an accelerometer and may be implemented utilizing all or portions of the structural and/or functional aspects of the methods and systems described in U.S. patent Application Publication 2021/0345891, filed May 8, 2020, entitled "METHOD AND DEVICE FOR DETECTING RESPIRATION ANOMALY FROM LOW FREQUENCY COMPONENT OF ELECTRICAL CARDIAC ACTIVITY SIGNALS"; U.S. patent Application Publication 2021/0350931, filed Mar. 8, 2021, entitled "METHOD AND SYSTEMS FOR HEART CONDITION DETECTION USING AN ACCELEROMETER", the complete subject matter which is expressly incorporated herein by reference in their entireties.

All references, including publications, patent applications and patents, cited herein are hereby incorporated by reference to the same extent as if each reference were individually and specifically indicated to be incorporated by reference and were set forth in its entirety herein.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order and/or iteratively and/or repetitively unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. An implantable medical device (IMD), comprising:

one or more electrodes configured to be implanted to define a pacing vector through at least a portion of a ventricle;

sensing circuitry configured to sense intrinsic atrial activity (As) and intrinsic ventricular activity (Vs);

a pulse generator (PG);

memory configured to store program instructions and an atrioventricular delay search parameter ($AVD_{SEARCH}$), wherein the $AVD_{SEARCH}$ is an interval of time; and one or more processors, that when executing the program instructions, is configured to:

direct the PG to deliver ventricular pacing pulses based on an atrioventricular delay (AVD);

periodically initiate an AVD search operation utilizing the $AVD_{SEARCH}$;

during the AVD search operation, determine a heart rate;

compare the heart rate to a threshold;

responsive to determining that the heart rate exceeds the threshold, reduce the $AVD_{SEARCH}$; and detect cardiac activity during the AVD search operation utilizing the reduced $AVD_{SEARCH}$.

2. The IMD of claim 1, wherein the $AVD_{SEARCH}$ is reduced by a predetermined duration for every beat per minute (bpm) that the heart rate exceeds the threshold, wherein the predetermined duration is stored in the memory.

3. The IMD of claim 1, wherein the one or more processors is further configured to store a rate-responsive sensitivity in the memory, wherein the $AVD_{SEARCH}$ IS reduced based on the rate-responsive sensitivity.

4. The IMD of claim 1, wherein the cardiac activity includes the Vs, wherein the one or more processors is further configured to, in response to identifying that fewer than a select number of cardiac beats exhibit the Vs during the AVD search operation, increase the reduced $AVD_{SEARCH}$.

5. The IMD of claim 1, wherein the one or more processors is further configured to:

identify whether the cardiac activity detected during the AVD search operation is indicative of a conduction block condition or non-conduction block condition; and in response to identifying the non-conduction block condition for a consecutive predetermined number of times, reduce the reduced $AVD_{SEARCH}$.

6. The IMD of claim 1, wherein the one or more processors is further configured to:

identify an intrinsic PR interval associated with the heart rate; and set the reduced $AVD_{SEARCH}$ to a greater one of i) the reduced $AVD_{SEARCH}$ and ii) the intrinsic PR interval plus a buffer length of time.

7. The IMD of claim 1, wherein the one or more processors is further configured to:

identify an intrinsic PR interval associated with the current heart rate; and set the reduced $AVD_{SEARCH}$ based on a comparison of the reduced $AVD_{SEARCH}$ and the intrinsic PR interval.

8. The IMD of claim 1, wherein the one or more processors is further configured to:

identify whether the cardiac activity detected during the AVD search operation is indicative of a conduction block condition or non-conduction block condition; and in response to identifying the conduction block condition, extend the reduced $AVD_{SEARCH}$.

9. The IMD of claim 8, wherein the one or more processors is further configured to extend the reduced $AVD_{SEARCH}$ up to a rate-dependent maximum.

10. A method for minimizing an atrioventricular delay search parameter ($AVD_{SEARCH}$), the method comprising:

providing one or more electrodes configured to be implanted to define a pacing vector through at least a portion of a ventricle;

providing sensing circuitry configured to sense intrinsic atrial activity (As) and intrinsic ventricular activity (Vs);

providing a memory configured to store program instructions and an $AVD_{SEARCH}$, wherein the $AVD_{SEARCH}$ is an interval of time; and utilizing one or more processors, in an implantable medical device (IMD), that when executing the program instructions during an AVD search operation, is configured for:

determining a current heart rate;

comparing the heart rate to a threshold;

responsive to determining that the heart rate exceeds the threshold, reducing the $AVD_{SEARCH}$; and detecting cardiac activity during an AVD search operation utilizing the reduced $AVD_{SEARCH}$.

11. The method of claim 10, wherein the $AVD_{SEARCH}$ is reduced by a predetermined number of milliseconds (ms) for every beat per minute (bpm) that the heart rate exceeds the threshold.

12. The method of claim 10, further comprising storing a rate-responsive sensitivity in the memory, wherein the $AVD_{SEARCH}$ is reduced based on the rate-responsive sensitivity, wherein the rate-responsive sensitivity is programmable.

13. The method of claim 10, wherein the cardiac activity includes the Vs, the method further comprising:

identifying a number of sensed ventricular events associated with the Vs detected during the AVD search operation; and in response to identifying that fewer than a select number of the sensed ventricular events are identified, increasing the reduced $AVD_{SEARCH}$.

14. The method of claim 10, further comprising:

identifying whether the cardiac activity detected during the AVD search operation is indicative of a conduction block condition or a non-conduction block condition; and in response to identifying the non-conduction block condition, reducing the extended $AVD_{SEARCH}$.

15. A system, comprising:

one or more electrodes configured to be implanted to define a pacing vector through at least a portion of a ventricle;

sensing circuitry configured to sense intrinsic atrial activity (As) and intrinsic ventricular activity (Vs);

a pulse generator (PG);

memory configured to store program instructions; and one or more processors, that when executing the program instructions, is configured to:

direct the PG to deliver ventricular pacing pulses based on an atrioventricular delay (AVD);

periodically initiate an AVD search operation in which the AVD is extended;

during the AVD search operation, monitor one or more interval stability characteristics; and suspend the AVD search operation based on the one or more interval stability characteristics.

16. The system of claim 15, wherein the interval stability characteristics include i) heart rate (HR), ii) HR variability, iii) posture, or iv) activity.

17. The system of claim 16, further comprising a physiological sensor configured to acquire data associated with at least one of the posture and activity.

18. The system of claim 15, wherein the one or more interval stability characteristics is a stability characteristic of a PR interval.

19. The system of claim 15, wherein the interval stability characteristics include a heart rate, wherein the one or more processors is configured to:

determine the heart rate; and compare the heart rate to a heart rate threshold stored in the memory, wherein the AVD search operation is suspended when the heart rate is below the heart rate threshold.

20. The system of claim 15, wherein the interval stability characteristics include a heart rate variability, wherein the one or more processors is configured to:

determine the heart rate variability; and compare the heart rate variability to a heart rate variability threshold stored in the memory, wherein the AVD search operation is suspended when the heart rate variability is below the heart rate variability threshold.

* * * * *